United States Patent
Kim et al.

(10) Patent No.: US 11,220,669 B2
(45) Date of Patent: *Jan. 11, 2022

(54) DEFINED THREE DIMENSIONAL MICROENVIRONMENT FOR CELL CULTURE

(71) Applicants: AMOLIFESCIENCE CO., LTD., Seoul (KR); Kollodis BioSciences, Inc., North Augusta, SC (US)

(72) Inventors: Chan Kim, Gwangju (KR); Kyuwon Baek, Seoul (KR); Hui-Gwan Goo, Seoul (KR); Sangjae Lee, Seoul (KR); Bongjin Hong, Pohang-si (KR); Song Hee Koo, Seoul (KR); In Yong Seo, Seoul (KR); Seung Hoon Lee, Paju-si (KR); Ji Hyun Lee, Incheon (KR); Seonho Jang, Seoul (KR); Dong-Sik Seo, Incheon (KR)

(73) Assignees: Amolifescience Co., Ltd., Seoul (KR); Kollodis BioSciences, Inc., North Augusta, SC (US)

( * ) Notice: Subject to any disclaimer, the term of this patent is extended or adjusted under 35 U.S.C. 154(b) by 124 days.

This patent is subject to a terminal disclaimer.

(21) Appl. No.: 15/953,055

(22) Filed: Apr. 13, 2018

(65) Prior Publication Data
US 2018/0237740 A1    Aug. 23, 2018

Related U.S. Application Data

(63) Continuation-in-part of application No. 15/173,488, filed on Jun. 3, 2016, now abandoned.

(60) Provisional application No. 62/171,767, filed on Jun. 5, 2015.

(51) Int. Cl.
    *C12N 5/00*     (2006.01)
    *C12N 5/0735*   (2010.01)

(52) U.S. Cl.
    CPC ......... *C12N 5/0062* (2013.01); *C12N 5/0075* (2013.01); *C12N 5/0606* (2013.01); *C12N 2501/998* (2013.01); *C12N 2513/00* (2013.01); *C12N 2533/30* (2013.01)

(58) Field of Classification Search
    None
    See application file for complete search history.

(56) References Cited

U.S. PATENT DOCUMENTS

| 7,615,373 | B2 | 11/2009 | Simpson et al. | |
| 8,728,818 | B2 * | 5/2014 | Sanyal | C12N 5/0068 435/402 |
| 9,006,394 | B2 | 4/2015 | Kiessling et al. | |
| 9,868,828 | B2 * | 1/2018 | Cho | C12N 5/0606 |
| 2006/0134050 | A1 | 6/2006 | Griffith et al. | |
| 2011/0039333 | A1 | 2/2011 | Kahn et al. | |
| 2016/0355780 | A1 | 12/2016 | Kim et al. | |

FOREIGN PATENT DOCUMENTS

| WO | WO 03/016351 | * | 2/2003 |
| WO | WO 2014/042463 | * | 3/2014 |

OTHER PUBLICATIONS

Takara Bio (downloaded from URL:< https://www.takarabio.com/assets/documents/User%20Manual/T100A_B_e.v1705.pdf> on Jan. 29, 2020) (Year: 2020).*
Hubbell et al. (Biomaterials 31 (2010) 1219-1226) (Year: 2010).*
Carson et al. (Regen Med. Jul. 2009 ; 4(4): 593-600) (Year: 2009).*
Ye et al. (Med Chem. Apr. 6, 2006; 49(7): 2268-2275) (Year: 2006).*
Shyu et al., Large-scale expansion of stem cells for therapy and screening, Stem Cells, Drug Discovery World, Winter 2013-14, pp. 35-39.
Legate, et al. "Genetic and cell biological analysis of integrin outside-in signaling" Genes Dev. 2009, 23, 397-418.
Mori et al. "Direct binding of integrin avβ3 to FGF1 plays a role in FGF1 signaling" J. Biol. Chem. 2008, 283, 18066-18075.
Krammer et al. "A structural model for force regulated integrin binding to fibronectin's ROD-synergy site" Matrix Biol 2002; 21: 139-147.

* cited by examiner

*Primary Examiner* — Sergio Coffa
(74) *Attorney, Agent, or Firm* — TraskBritt

(57) ABSTRACT

Described is a three-dimensional (3D) microenvironment presenting defined biochemical and physical cues that regulate cellular behavior and use of the microenvironment. A composition to form the 3D microenvironment is provided by combining one or more natural or synthetic polymeric materials and substrate proteins recombinantly or chemically functionalized with a variety of bioactive peptides such as extracellular matrix-derived or growth factor-derived peptides. Also described are devices and methods for screening for optimal combinations of the bioactive motifs in order to create an extracellular microenvironment that can regulate specific cellular behavior such as cell growth, proliferation, migration or differentiation.

1 Claim, 22 Drawing Sheets
(19 of 22 Drawing Sheet(s) Filed in Color)

Specification includes a Sequence Listing.

DEFINED THREE DIMENSIONAL MICROENVIRONMENT FOR CELL CULTURE

CROSS-REFERENCE TO RELATED APPLICATION

This application is a continuation-in-part of co-pending U.S. patent application Ser. No. 15/173,488, filed Jun. 3, 2016, which itself claims the benefit of the filing date of U.S. Provisional Patent Application Ser. No. 62/171,767, filed Jun. 5, 2015, the disclosure of each of which is hereby incorporated herein in its entirety by this reference.

TECHNICAL FIELD

This application relates to synthetic microenvironment for culturing cells such as valuable cells including stem cells such as pluripotent stem cells. More particularly, provided are methods and microenvironmental surfaces for culturing pluripotent stem cells, adult stem cells, and adult cells on a defined three-dimensional microenvironment.

STATEMENT ACCORDING TO 37 C.F.R. § 1.821(c) or (e)—SEQUENCE LISTING SUBMITTED AS ASCII TEXT FILE

Pursuant to 37 C.F.R. § 1.821(c) or (e), a file containing an ASCII text version of the Sequence Listing has been submitted concomitant with this application, the contents of which are hereby incorporated by reference.

BACKGROUND

An extracellular microenvironment, as defined by biochemical cues and physical cues and supporting cells, plays a central role in the regulation of cellular behavior including cell attachment, spreading, migration, growth, proliferation and differentiation.

Extracellular matrix ("ECM"), growth factor, and cytokine signaling environments are the important mechanisms for regulating cell fate, and these microenvironmental stimuli are processed through combinatorial signaling pathways. The interactions between signaling pathways are critical in determining cell fate (C. J. Flaim et al., *Stem Cells Dev.* 2008, 17(1):29-39).

Most cells including pluripotent & multipotent stem cells, and adult cells in tissues are surrounded on all sides by a complex set of extracellular matrix (ECM) proteins that are critical in guiding cell function. Cells bind to the ECM via specific cell surface receptors such as integrin receptors, and this binding serves as a biochemical cue that can directly affect cell function. In addition, the ECM acts as a modulator of biochemical and mechanical stimuli that are present in tissues. For example, ECM proteins can sequester and release growth factors, control the rate of nutrient supply, as well as control cell shape and transmit mechanical signals to the cell surface.

Understanding the principles and mechanism that underlie cell regulation or fate determination is central to realize clinical application of cell therapy, especially for stem cell based therapy or tissue engineering application.

Embryonic Stem Cells (ESCs) or induced pluripotent stem cells (iPSs) are capable of differentiating into any cell type of the body while adult stem cells such as mesenchymal stem cell are more limited in their ability to differentiate into different lineages, emerging evidence has shown that they have the ability to generate unrelated cell types via genetic reprogramming (see, L. Bouwens et al., The use of stem cells for pancreatic regeneration in diabetes mellitus, *Nat. Rev. Endocrinol.* 2013, 9(10):598-606; R. C. Addis et al., Induced regeneration—the progress and promise of reprogramming for heart repair, *Nat. Med.* 2013, 19(7):829-836). The stem cells represent highly promising cell sources for numerous biomedical applications, such as cell replacement therapies, tissue and organ engineering, and pharmacology and toxicology screens. Stem cell maintenance, proliferation and expansion are important for the applications above.

Generally a feeder composed of monolayers of inactivated fibroblast cells or reconstituted basement membrane such as Matrigel™ (BD Biosciences) or GelTrex™ (Life Technologies) are required to maintain self-renewal and pluripotentcy of embryonic stem cell or induced pluripotent stem cells (iPS) in media containing serum or serum replacement. These conditions include animal component and it has been reported that hESC cultured under these conditions acquired a non-human mammalian sialic acid, Neu5Gc (see, U.S. Patent Publication No. US20110039333, the contents of which are incorporated herein by this reference). These conventional substrates have significant lack of batch-to-batch or lot-to-lot consistency, resulting in experimental variability.

Various methods or surfaces have been developed to overcome the challenges described above. For example, a gelatin-coated surface in the presence of secreted factors from feeder cells, allowing the cells to be cultured in the absence of feeder cell layers (i.e., feeder-free). For example, feeder cell layers can be avoided through the use of "conditioned medium" (CM) (see, C. Xu et al., "Feeder-free growth of undifferentiated human embryonic stem cells," *Nat. Biotechnol.* 19:971-974 (2001)).

Additionally, current two-dimensional (2D)-based cell culture systems, which suffer from inherent heterogeneity and limited scalability and reproducibility, are emerging as a bottleneck for producing sufficient numbers of high-quality cells for downstream applications. An attractive approach for scaling up production is to move cell culture from 2D to 3D, and accordingly several 3D suspension systems have been probed for hPSCs production: cell aggregates, cells on microcarriers, and cells in alginate microencapsulates.

A major challenge remains with the in vitro expansion and culture of self-renewable stem cells and the subsequent differentiation of these cells. Recently, several protocols have been reported that alter culturing conditions and other factors (e.g., medium and design of cell culture vessel) that support reliable amplification of immature and differentiated stem cells. However, challenges still exist in optimizing the wide variety of platforms capable of supporting cell therapy needs.

The self-renewal and pluripotency of murine ESCs (mESCs) and human ESCs (hESCs) are regulated by a combination of extrinsic and intrinsic factors. The factors regulate signaling pathway to control pluripotency transcription factors such as Oct4, Sox2, and Nanog (see, J. A. Thomson et al. (1998), Embryonic stem cell lines derived from human blastocysts, *Science* 282(5391):1145-1147).

The hESCs show activated Nodal/Activin, FGF and WNT pathways and have the potential for long-term maintenance in undifferentiated state and generation of three germ layer derivatives (Sato et al., 2004; Thomson et al., 1998; Xiao et al., 2006). FGF2 promotes self-renewal of hESCs by activating the PI3K/Akt activation to promote cell proliferation, growth, motility, and survival. WNTs (wingless-type MMTV integration site family members) proteins also play an important role in controlling ESC maintenance.

Stem cells reside in a specialized microenvironment, stem cell niche, which provides extracellular cues to allow stem cell survival and to maintain a balance between self-renewal and differentiation. Extracellular matrix (ECM) proteins that bind to mainly integrin are key components shaping the niche and maintaining stem cell homoeostasis. Integrin crosstalk with other receptors regulates signaling Erk ½, Akt, or SMAds responsible for preserving sternness. Integrins can potentiate signaling pathways in response to growth factors, cytokines such as IL-3 or TGF-beta, essential ligands cell self-renewal or pluripotency of hESCs (see, M. F. Brizzi et al., Extracellular matrix, integrins, and growth factors as tailors of the stem cell niche, 2012 *Current Opinion in Cell Biology*, Volume 24, Issue 5, 645-651).

Extracellular microenvironments, defined by biochemical cues and physical or mechanical cues, are a deciding factor in a wide range of cellular processes including cell adhesion, proliferation, differentiation, and expression of phenotype-specific functions (see, D. E. Discher et al., *Science*, 2009, 26; 324 (5935):1673-7; and R. O. Hynes, *Trends Cell Biol.* 1999, 9(12):M33-7).

Most cells in tissues are surrounded on all sides by a complex set of extracellular matrix (ECM) proteins that are critical in guiding cell function. Cells bind to the ECM via specific cell surface receptors such as integrin receptors, and this binding serves as a biochemical cue that can directly affect cell function. In addition, the ECM acts as a modulator of biochemical and mechanical stimuli that are present in tissues. For example, ECM proteins can sequester and release growth factors, control the rate of nutrient supply, as well as control cell shape and transmit mechanical signals to the cell surface.

ECM and growth factor signaling environments are the important mechanisms for regulating cell fate; and, these microenvironmental stimuli are processed through combinatorial signaling pathways. The interactions between signaling pathways are critical in determining cell fate including stem cells (C. J. Flaim et al., *Stem Cells Dev.* 2008, 17(1):29-39).

Complexities associated with native extracellular matrix proteins, including complex structural composition, purification, immunogenicity and pathogen transmission have driven the development of synthetic biofunctionals for use as 2D (two-dimensional) or 3D (three-dimensional) extracellular microenvironments in order to mimic the regulatory characteristics of natural ECMs and ECM-bound growth factors (M. P. Lutolf et al., *Nat. Biotechnol.* 23(1):47-55 (2005); and K. Ogiwara et al., *Biotechnol. Lett.* 27(20): 1633-7 (2005)).

Many attempts have been made to create a synthetic 2D or 3D extracellular microenvironment by incorporating cell adhesion ligands into synthetic surfaces. Biologically derived or synthetic materials have been explored as an extracellular microenvironment to gain control over the material and thus over the cellular behavior they induced. One example is a crosslinkable hyaluronic acid, alginate or polyethylene glycol based hydrogel with an RGD peptide motif grafted onto the polymer backbone (Woerly et al., *J. Neural Transplant. Plasticity,* 1995, 5:245-255; Imen et al., *Biofunctionals,* 2006, 27, pp. 3451-3458; U.S. Pat. No. 20060134050).

U.S. Pat. No. 8,728,818, the contents of which are incorporated herein by this reference, disclosed a defined surface that presents ECM-derived peptide motifs to activate integrin to support self-renewal and pluripotency of stem cell. U.S. Pat. No. 9,006,394, the contents of which are incorporated herein by this reference, disclosed a peptide presenting surface to support long-term self-renewal of human embryonic stem cell. The peptide is heparin-binding domain from vitronectin, fibronectin or from bone sialoprotein. The surfaces in these patents require soluble factors such as FGF or ROCK inhibitor to support long-term self-renewal and pluripotency of ESCs.

However, existing technologies have some limitations to generate a microenvironment that induces a combinatorial signal pathway by selectively, simultaneously or sequentially activating at least two different cell surface receptors in a precisely manner, due to their lack of physical or biochemical attributes. In addition, various microenvironmental cues are often intertwined and cannot be individually controlled in existing technologies.

BRIEF SUMMARY

We have developed a biochemically and physically defined 3D microenvironment that mimics native extracellular microenvironments by presenting combinatorial receptor-ligand interactions with controlled physical cues including surface morphology and fiber diameter. Our engineered 3D microenvironment can be used as an array of cell culture environments for screening of cell culture or tissue engineering environment by elucidating or regulating cellular behaviors such as cell adhesion, migration, growth, proliferation or morphogenesis as evidenced in stem cell assays.

Provided is a microenvironmentally defined surface that can promote signaling pathway to generate WNT/β-catenin, FGF/MEK, TGF-STAT, or LIF/STAT3 to support stem cell culture in serum- and feeder-free conditions.

In one aspect, provided is a 3D microenvironment surface that induces integrin signaling to promote signal pathway for self-renewal or proliferation of pluripotent stem cell in serum- or feeder-free conditions. It is well known that integrin signaling involves Erk activation and self-renewal of embryonic stem cell is mediated signal through Ras-Raf-MEK-Erk cascade.

Simultaneous ligation of four integrin heterodimers (α5β1, α6β1, α9β1, and αvβ5) promoted self-renewal (see, Seung Tae Lee et al., Engineering integrin signaling for promoting embryonic stem cell self-renewal in a precisely defined niche, *Biomaterials* 31 (2010) 1219-1226). But in the disclosure, integrin activation of α5β1 binding motif alone or in combination with α6β1 binding motif is sufficient to generate the signaling for self-renewal and proliferation of pluripotent stem cell in the serum-free and feeder free defined conditions.

In another aspect, a biochemically defined microenvironment that induces integrin and fibroblast growth factor receptors simultaneously or sequentially to promote signal pathway for self-renewal or proliferation of pluripotent stem cell in serum- or feeder-free conditions is provided.

In another aspect, a combinatorial microenvironment comprising a nanofibrous substrate having an average diameter of 100 to 2000 nm, wherein the nanofibrous surface presents extracellular matrix mimetic, growth factor mimetic, WNT mimetic, cytokines mimetic, LIF mimetic or its combination is provided.

In other aspects, provided is a method of preparing a cell culturing substrate, the method including: providing a biochemically defined surface, wherein integrin activating peptide motif are coated to form a biochemical defined surface for cell culture in a defined condition; the peptide motif can activate integrin α5β1- and/or α6 β1-integrins to generate integrin-mediated signaling simultaneously or sequentially.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In FIG. 4A, cell B1 is SEQ ID NO:47 (residues 1-15); cell B2 is SEQ ID NO:48 (residues 1-15); cell B3 is SEQ ID NO:49; cell B4 is SEQ ID NO:50 (residues 1-15); cell C1 is SEQ ID NO:15; cell C2 is SEQ ID NO:17; cell C3 is SEQ ID NO:18; cell C4 is SEQ ID NO:19. In FIG. 4B, cell A1 is SEQ ID NO:20; cell A2 is SEQ ID NO:56; cell A3 is SEQ ID NO:34; cell A4 is SEQ ID NO:33; cell B1 is SEQ ID NO:21; cell B2 is SEQ ID NO:57; cell B3 is SEQ ID NO:51 (residues 1-6, 8-10); cell B4 is SEQ ID NO:22; cell C1 is SEQ ID NO:23; cell C2 is SEQ ID NO:58; cell C3 is SEQ ID NO:24; cell C4 is SEQ ID NO:25. In FIG. 4C, cell A1 is SEQ ID NO:26; cell A2 is SEQ ID NO:27; cell A3 is SEQ ID NO:28; cell A4 is SEQ ID NO:29; cell B1 is SEQ ID NO:30; cell B2 is SEQ ID NO:31; cell B3 is SEQ ID NO:32; cell C1 is SEQ ID NO:52 (residues 1-2, 4-10); cell C2 is SEQ ID NO:53; cell C3 is SEQ ID NO:54; cell C4 is SEQ ID NO:55.

FIG. 5A represents the colony of mESC cultured on nanofibrous substrate and the colony of mESC on nanofiber having particles in FIG. 5B. The surface presenting PHSRN-RGDSP (SEQ ID NO:17) that can activate integrin α5β1 to effectively support self-renewal and proliferation of embryonic stem cell provided more favorable environment so that the size of colony is larger than in other surfaces. In FIG. 5A, cell B1 is SEQ ID NO:47; cell B2 is SEQ ID NO:48; cell B3 is SEQ ID NO:49; cell B4 is SEQ ID NO:50; cell C1 is SEQ ID NO:15; cell C2 is SEQ ID NO:17; cell C3 is SEQ ID NO:18; cell C4 is SEQ ID NO:19. In FIG. 5B, cell A1 is SEQ ID NO:20; cell A2 is SEQ ID NO:56; cell A3 is SEQ ID NO:34; cell A4 is SEQ ID NO:33; cell B1 is SEQ ID NO:21; cell B2 is SEQ ID NO:57; cell B3 is SEQ ID NO:51; cell B4 is SEQ ID NO:22; cell C1 is SEQ ID NO:23; cell C2 is SEQ ID NO:58; cell C3 is SEQ ID NO:24; cell C4 is SEQ ID NO:25. In FIG. 5C, cell A1 is SEQ ID NO:26; cell A2 is SEQ ID NO:27; cell A3 is SEQ ID NO:28; cell A4 is SEQ ID NO:29; cell B1 is SEQ ID NO:30; cell B2 is SEQ ID NO:31; cell B3 is SEQ ID NO:32; cell C1 is SEQ ID NO:52; cell C2 is SEQ ID NO:53; cell C3 is SEQ ID NO:54; cell C4 is SEQ ID NO:55.

FIG. 7A contains SEQ ID NOS:37-41, 45, 46, and 73. Specifically, with reference to the bFGF mimetic peptide portion of FIG. 7A, column 1 row 1 is SEQ ID NO:37; column 1 row 2 is SEQ ID NO:39; column 1 row 3 is SEQ ID NO:41; column 2 row 1 is SEQ ID NO:38; column 2 row 2 is SEQ ID NO:40; column 2 row 3 is SEQ ID NO:73. With reference to the TGFβ mimetic peptide of FIG. 7A, the top figure is SEQ ID NO:45, and the bottom figure is SEQ ID NO:46. With reference to FIG. 7B, column 1 row 1 is SEQ ID NO:37; column 1 row 2 is SEQ ID NO:39; column 1 row 3 is SEQ ID NO:41; column 2 row 1 is SEQ ID NO:38; column 2 row 2 is SEQ ID NO:40; column 2 row 3 is SEQ ID NO:73. With reference to the TGFβ mimetic peptide of FIG. 7A, the top figure is SEQ ID NO:45, and the bottom figure is SEQ ID NO:46.

FIG. 8A showed the comparison of 2D and 3D (WebTrix™) microenvironment effect on stemness maintenance and colony size under the same microenvironment surface. 3D culture showed the better colony shape than 2D culture. FIG. 8B showed the effect of various microenvironmental signaling on the stem cell cultured on integrin-GF receptor, integrin-GF receptor and cytokine (WNT/LIF) receptor. The best results came from the combination of Integrin-FGF receptor-TGFβ and Integrin-FGF receptor-frizzed receptor (WNT5a). FIGS. 8C and 8D showed the effect of signaling ratio induced by different composition of PHSRN-RGDSP (SEQ ID NO:17)/WNT5A and PHSRN-RGDSP (SEQ ID NO:17)/LIF, respectively. FIGS. 8E and 8F showed the analysis of stemness marker and differentiation marker expression, respectively.

With reference to FIG. 11B, and in order from left to right (starting with "control"), each of the sequences correspond to SEQ ID NO:80, SEQ ID NO: 81, SEQ ID NO:82, SEQ ID NO:79, SEQ ID NO:78, SEQ ID NO:74, SEQ ID NO:75, SEQ ID NO:76, and SEQ ID NO:77.

DETAILED DESCRIPTION

Figure 1:
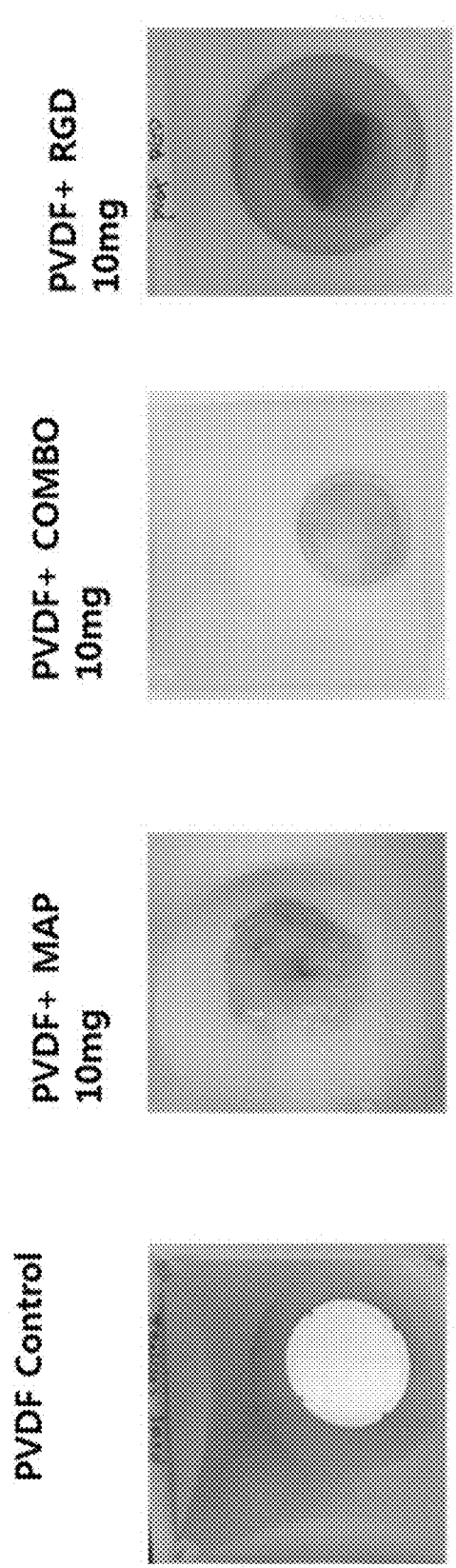
FIG. 1 represents nanofibrous substrate as a synthetic 3D microenvironment. Each nanofiber has 200, 500 and 800 nm diameter.

This disclosure is directed to engineered extracellular microenvironments that mimic biochemically and/or physically natural extracellular microenvironments.

A microenvironment comprising at least one of binding motifs selected from the group consisting of adhesion receptor binding motifs and/or co-receptor binding motifs, wherein the binding motifs regulate cellular behavior via combinatorial signaling generating from crosstalk between adhesion receptors, adhesion receptor-co-receptor, co-receptors, or combination thereof, wherein the adhesion receptor binding motif is derived from at least one or more selected from the group consisting of extracellular matrix proteins and cadherin, or its mimetic and wherein co-receptor binding motif is derived from at least one or more selected from the group consisting of cadherin, growth factors, and cytokines. Specifically, the adhesion receptor binding motifs may include an integrin binding motifs, and the adhesion receptor binding motifs is derived from extracellular matrix proteins, cadherin or those mimetics. Also, co-receptor binding motif is derived from cadherin, growth factors or cytokines.

The adhesion receptor binding motifs may comprise at least one or more selected from the group integrin binding motifs and cadherin binding motifs.

Wherein the adhesion receptor binding motif comprises at least one or more selected from the group consisting of integrin α5β1, α6β1 or αvβ3 binding motifs or E-cadherin, N-cadherin, P-cadherin binding motif.

Wherein the adhesion receptor binding motif comprises an integrin α5β1 binding motif. And the integrin α5β1 binding motif comprises a RGD (SEQ ID NO:15) containing peptide, wherein the RGD containing peptide comprises PHSRN-RGDSP (SEQ ID NO:17).

Further, the adhesion receptor binding motif may comprise an integrin α6β1 binding motif, and wherein the integrin α6β1 binding motif may comprise at least one or more selected from the group consisting of laminin α1 LG domain-derived motif, laminin α5 LG domain-derived motif, and γ1 chain-derived motif. Wherein the integrin α6β1 binding motif comprises at least one or more selected from the group consisting of NRWHSIYITRFG (SEQ ID NO:34), GKNTGDHFVLYM (SEQ ID NO:22), VVSLYNFEQTFML (SEQ ID NO:23), VLVRVERATVFS (SEQ ID NO:27), and RNIAEIIKDI (SEQ ID NO:51).

This may include the co-receptor binding motifs and the co-receptor motifs may comprise at least one or more selected from the group consisting of cadherin binding motif, growth factor receptor binding motif and cytokine binding motif.

The co-receptor binding motif may comprise cadherin binding motifs, wherein the cadherin binding motif comprises at least one or more selected from the group consisting of LFSHAVSSNG (SEQ ID NO:52), ADTPPV (SEQ ID NO:53), DQNDN (SEQ ID NO:54) and LRAHAVDING (SEQ ID NO:55).

Further, wherein the co-receptor binding motif may comprise growth factor receptor binding motif. Wherein the growth factor receptor binding motif is selected from fibroblast growth factor (FGF)- or transforming growth factor (TGF)-receptor binding motif.

Provided is a microenvironment, wherein the FGF receptor binding motif is at least one or more selected from the group consisting of TGQYLAMDTDGLLYGS (SEQ ID NO:35), WFVGLKKNGSCKRG (SEQ ID NO:36), ANRYLAMKEDGRLLAS (SEQ ID NO:37), ERGVVSIKGV (SEQ ID NO:38), WYVALKRTGQYKLG (SEQ ID NO:39), HFKDPKRLYCK (SEQ ID NO:40), FLPMSAKS (SEQ ID NO:41), KTGPGQKA (SEQ ID NO:42), SRFFVAMSSKGKLYGS (SEQ ID NO:43) and MFIALSKNGKTKKG (SEQ ID NO:44).

The TGF receptor binding motif may comprise at least one or more selected from the group consisting of LTGKNFPMFHRN (SEQ ID NO:45) and MHRMPSFLPTTL (SEQ ID NO:46).

Further, wherein the co-receptor biding motif of the microenvironment may comprises cytokine binding motif and the cytokine binding motif may comprise at least one or more selected from the group comprising WNT-derived peptide motif and LIF-derived peptide motif. Further to the WNT-derived peptide motif may comprise at least one or more selected from the group consisting of LCCGRGHRTRTQRVTERCNC (SEQ ID NO:47) and LGTQGRLCNKTSEGMDGCEL (SEQ ID NO:48). The LIF-derived motif comprises at least one or more selected from the group consisting of IVPLLLLVLH (SEQ ID NO:49) and YTAQGEPFPNNVEKLCAP (SEQ ID NO:50).

Provided is a biomaterial composition for electrospun matrix, comprising a) a synthetic hydrophobic polymer for electrospinning, b) hydrophilic protein comprising at least one or more selected from the group consisting of integrin binding motif, cadherin binding motif, growth factor receptor binding motif, and cytokine receptor binding motif at C-, N-, or C- and N-terminus of the hydrophilic protein. The hydrophobic polymer may be a polyvinylidene fluoride (PVDF).

The hydrophilic protein comprises proteins comprising at least one or more selected from the group consisting of SEQ ID NO:1 to SEQ ID NO:14NO:14.

Provided is a three-dimensional microenvironment for growing, self-renewing, or proliferating stem cells comprising:
  a) an electrospun nanofiber matrix that comprises a hydrophilic protein comprising at least one or more binding motifs selected from the group consisting of integrin-, cadherin-, growth factor receptor, and cytokine receptor binding motifs; and
  b) chemically defined media,
  wherein the binding motif surfaced on a hydrophobic polymer supports growth and self-renewal of a stem cell.

The hydrophilic protein further comprises at least one or more antimicrobial peptide motif is immobilized on the substrate.

The antimicrobial peptide is at least one or more selected from the group consisting of KLWKKWAKKWLKLWKA (SEQ ID NO:59), FALALKALKKL (SEQ ID NO:60), ILRWPWWPWRRK (SEQ ID NO:61), AKRHHGYKRKFH (SEQ ID NO:62), KWKLFKKIGAVLKVL (SEQ ID NO:63), LVKLVAGIKKFLKWK (SEQ ID NO:64), WSILAPLGTTLVKLVAGIGQQKRK (SEQ ID NO:65), GIGAVLKVLTTGLPALISWI (SEQ ID NO:66), SWLSKTAKKGAVLKVL (SEQ ID NO:67), KKLFKKILKYL (SEQ ID NO:68), GLKKLISWIKRAAQQG (SEQ ID NO:69) and GWLKKIGKKIERVGQHTRDATIQGLGIAQQAANVAATAR (SEQ ID NO:70).

Also provided is biochemically and physically defined surface that regulates cell surface receptors specifically, selectively, simultaneously, or sequentially to regulate cellular behavior such as cell attachment, migration, growth, proliferation, or differentiation of cells.

Also provided is microenvironments that comprise at least one or more selected from the group consisting of integrin binding motif, cadherin binding motif, growth factor receptor and cytokine binding motif.

As used herein "microenvironment" refers to physical and/or biochemical cues, surrounding a cell in an organism or in the laboratory. Molecules, including small molecules such as compounds and soluble factors, macromolecules such as insoluble polymers, nutrients, growth factors, fluids, cytokines and parameters such as pH, ionic strength and gas composition, and the like surrounding the cell are the biochemical cues. The molecules for biochemical cues may be, reversibly or irreversibly in response to biological or physiological conditions, immobilized to the substrate.

A microenvironmentally, namely biochemically and physically, defined cell culturing substrate is provided for regulating cellular behavior in serum-free and feeder-free conditions for extended periods of time in culture. The microenvironmentally defined culture surface hereof promotes more efficient attachment and expansion of cells such as pluripotent stem cells as well as adult stem cells such as mesenchymal or neural stem cells in an undifferentiated state, as compared to standard culture substrates such as tissue culture-treated or serum coated surfaces. In some embodiments, human embryonic or induced pluripotent cells may be expanded on the microenvironmentally defined cell culture surface.

Biochemically defined surface is a surface that presents ECM-, growth factor-, or cytokine-derived peptide motif or its mimetic, alone or in combination, to mimic in vivo microenvironment in order to regulate cellular behaviors.

ECM, growth factor, or cytokine signaling environments are the important mechanisms for regulating cell fate; and, these microenvironmental stimuli are processed through combinatorial signaling pathways. The interactions between signaling pathways are critical in determining cell fate (C. J. Flaim et al., *Stem Cells Dev.* 2008, 17(1):29-39).

The biochemically defined, peptide motif-presenting surfaces described herein are useful in a variety of contexts and applications. For example, for stem cell culture, the defined surfaces can be used for maintaining pluripotent cells in an undifferentiated state. In addition, the surfaces can be used for expanding a population of pluripotent cells without loss of differentiation potential in serum free or feeder-free conditions. The biochemically defined, peptide-presenting surfaces are also useful for culturing pluripotent cells that are subsequently induced to differentiate by, for example, adding one or more differentiation agent to the media. Differentiated cells derived from pluripotent cells can be maintained on the biochemically defined surfaces.

Suitable pluripotent cells for use herein include ESCs and iPS cells, which preferably are from a primate, especially a human primate. As used herein, "embryonic stem cells" or "ESCs" mean a pluripotent cell or population of pluripotent cells derived from an inner cell mass of a blastocyst.

Suitable adult stem cells for use herein include mesenchymal stem cell, neural stem cell, hematopoietic stem cell, which preferably are from a primate, especially a human primate.

Suitable adult cells for use herein include, primary or cell lines such as immortalized HUVEC cells, epithelial cell, endothelial cell, neural cell, mesenchymal cell, etc.

Regardless of the cell used, the biochemically defined surfaces described herein can be constructed according to known methods. For example, one can use contact spotting of peptides onto glyoxylyl-functionalized glass slides (see, e.g., J. Falsey et al., "Peptide and small molecule microarray for high throughput cell adhesion and functional assays," *Bioconjug. Chem.* 12, 346-353 (2001)); contact printing of peptides onto acrylamide-coated glass slides; and spotting combinations of peptides onto a glass slide followed by in situ polymerization (see, e.g., Anderson et al., Nanoliter-scale synthesis of arrayed biomaterials and application to human embryonic stem cells, *Nat. Biotechnol.* 22:863 (2004). In addition, one can use streptavidin-coated plates treated with a biotinylated peptide of interest or even polyacrylamide gels cross-linked to a peptide of interest. See, e.g., Klein et al., Cell adhesion, cellular tension, and cell cycle control, *Meth. Enzymol.* 426:155 (2007).

The biochemically defined surface presents a plurality of adhesion receptor binding peptide motifs and a plurality of co-receptor binding peptide motifs to activate at least two different receptors of cells. The adhesion receptor binding peptide motifs can bind to integrin or cadherin, and the co-receptor binding peptide motif activates to co-receptor such as growth factor receptor or cytokine receptor that coordinates with the adhesion receptor signaling.

Integrin, cadherin, and growth factor receptor mediated signaling are essential for fundamental cellular functions including cell adhesion, migration, proliferation, differentiation, and survival. These cell surface receptors cross-talk with each other in the regulation of such cellular functions.

Typical examples are integrin-integrin and integrin-cadherin crosstalk. Crosstalk between integrins has been well known in immune system and angiogenesis. For example, in human lymphocytes, $\alpha L\beta 2$ (LFA-1) integrin binding to ICAM-1 decreases adhesion of $\alpha 4\beta 1$ integrin to VCAM-1 and fibronectin, facilitating detachment of $\alpha 4\beta 1$ integrin from the apical surface of endothelial cells. The decreased $\alpha 4\beta 1$ integrin activity leads to an enhancement of $\alpha 5\beta 1$ integrin mediated migration on fibronectin, a process that promotes transmigration through an endothelium (J. C. Porter, N. Hogg, Integrin cross talk: activation of lymphocyte function-associated antigen-1 on human T cells alters alpha4beta1- and alpha5beta1-mediated function, *J. Cell Biol.* 1997, 138(6):1437-47). The coordinate modulation of the cellular functions of cadherins and integrins plays an essential role in fundamental physiological and pathological processes, including morphogenesis, tissue differentiation and renewal, wound healing, immune surveillance, inflammatory response, tumor progression, and metastasis (see, Luca Goitre et al., *Journal of Signal Transduction Volume* 2012 (2012), 12 pages).

For another example, it has been known that crosstalk between integrins and growth factor receptors by two mechanism, i) two separate signals merge with one another in multiple levels inside the cells (see, Legate, et al., Genetic and cell biological analysis of integrin outside-in signaling, Genes Dev. 2009, 23, 397-418), or ii) FGF1 directly binds to integrin $\alpha v\beta 3$ in order to induces the FGFR1-FGF1-integrin $\alpha v\beta 3$ ternary complex (S. Mori et al., Direct binding of integrin $\alpha v\beta 3$ to FGF1 plays a role in FGF1 signaling, *J. Biol. Chem.* 2008, 283, 18066-18075). In one embodiment, the extracellular microenvironment surface simultaneously activates two different receptors integrin $\alpha 5\beta 1$ and FGFR to support self-renewal of pluripotent or multi-potent stem cell.

An extracellular component such as a cell adhesion molecule such as ECM protein or cadherin, growth factors, or cytokines can be a natural or recombinant extracellular matrix protein, ECM- or cadherin-derived domain including core motif that binds to specific adhesion receptor such as integrin or cadherin or its mimetic, growth factor (GF)-derived domain containing core motif that bind to specific binding sites of such growth factor receptor, or its mimetic, and cytokine-derived domain containing core motif that binds to cytokine receptor, or its mimetic. The mimetic comprises of a recombinant protein or polypeptide functionalized with at least one or more peptide motifs derived from a variety of extracellular components described above.

Any suitable natural extracellular matrix proteins including but not limited to fibronectin, laminin, vitronectin may be used as an extracellular component to activate integrins. Preferably, the extracellular matrix protein is fibronectin. More preferably, the fibronectin can be used alone or the combination with laminin, vitronectin or cadherin.

Any suitable natural or recombinant cadherin such as E-cadherin or N-cadherin may be used as an extracellular component to activate adhesion receptors. Preferably, the cadherin is E-cadherin.

Any suitable natural growth factors are fibroblast growth factor (FGF) or transforming growth factor (TGF) may be used as an extracellular component to activate such growth factor receptors. Preferably, the growth factor can be used along or the combination of FGF and TGF.

Generally any extracellular mimetic component including extracellular matrix mimetic, cadherin mimetic, growth factor mimetic, or cytokine mimetic comprises a substrate protein recombinantly or chemically functionalized with peptide motif derived from the extracellular components.

Any suitable substrate protein including but not limited to fibrin, elastin, mussel adhesive protein may be used as the substrate protein to present extracellular component. Preferably, the protein is a recombinant mussel adhesive protein.

Any suitable recombinant mussel adhesive protein may be used as the extracellular component herein. Examples of commercially available substrate proteins include MAP-Trix™ ECM marketed by Kollodis BioSciences, Inc. (North Augusta, S.C.). An optional third component is a biocompatible polymer (e.g., polyethylene glycol or polyvinylalcohol), which may be added to the compositions to enhance their physicomechanical characteristics such as physical or mechanical properties of a customizable microenvironment.

The MAPTrix™, developed by Kollodis BioSciences Inc. (North Augusta, S.C.), are predesigned mussel adhesive protein or barnacle-based extracellular component mimetics. The mussel adhesive proteins were recombinantly functionalized with a variety of ECMs-, GFs-, or other ligand-derived peptides in order to mimic the bioactivity of naturally occurring ligands such as ECMs, GFs, or cytokines including, but not limited to, IL-3, LIF, or WNT which were demonstrated to have a similar bioactivity to natural or recombinant ECMs, GFs, or cytokines in primary cell cultures as compared to various natural or recombinant ECM, GF or cytokine proteins. The pre-designed MAPTrix™ mimetics are highly advantageous for creating extracellular microenvironments. For example, it provides for the design of cell-specific or user-defined regulation of extracellular microenvironments to emulate the native microenvironment in terms of biochemical cues.

The MAPTrix™ is a fusion protein comprising a first peptide of mussel foot protein FP-5 that is selected from the group consisting SEQ ID NOS:1-4, or barnacle-derived adhesive protein consisting SEQ ID NO:5 and a second peptide of at least one selected from the group consisting of mussel FP-1 selected from the group consisting of SEQ ID NOS:6-8, mussel FP-2 (SEQ ID NO:9), mussel FP-3 selected from the group consisting of SEQ ID NOS:10-11, mussel FP-4 (SEQ ID NO:12), mussel FP-6 (SEQ ID NO:13) and fragment thereof, and the second peptide is linked to C-terminus, N-terminus or C- and N-terminus of the FP-5. Preferably, the second peptide is the FP-1 comprising an amino acid sequence of SEQ ID NO:6.

Extracellular components including integrin binding motif or co-receptor binding motif such as fibroblast growth factor receptor (FGFR), transforming growth factor receptor (TGFR), insulin-like growth factor receptor (IGFR)-derived peptide motif, cytokine receptor binding motif such as WNT and/or LIF (leukemia inhibitor factor)-derived core motif may also be incorporated into the mussel adhesive protein to further enhance the beneficial effect of the extracellular environment mimic on self-renewal and pluripotency of a stem cell.

There are 24 known integrin heterodimers comprised of one of 18α subunits and one of 8β subunits and these have a diverse range of functions mediating cell-cell adhesion, growth factor receptor responses and intracellular signaling cascades for cell migration, differentiation, survival and proliferation. A number of ECM molecules or domains are capable of assisting in the maintenance of undifferentiated hESC alone or in combination, including laminin 511 (see, T. Miyazaki et al., Recombinant human laminin isoforms can support the undifferentiated growth of human embryonic stem cells, *Biochem. Biophys. Res. Commun.*, 375 (2008), pp. 27-32), fibronectin and vitronectin (see, Melkoumian et al., Synthetic peptide-acrylate surfaces for long-term self-renewal and cardiomyocyte differentiation of human embryonic stem cells, *Nat. Biotechnol.* 28 (2010), pp. 606-610; Braam et al., Recombinant vitronectin is a functionally defined substrate that supports human embryonic stem cell self-renewal via alphavbeta5 integrin, *Stem Cells* 26 (2008), 2257-2265).

The extracellular domain of integrins can bind ECM proteins used in hESC support such as collagen, fibronectin, laminin and vitronectin as well as members of the SIBLING family (Small Integrin Binding Ligand, N-Linked Glycoproteins, e.g., osteopontin and bone sialoprotein). Integrin clustering occurs after ECM adhesion promoting lateral association with other cell surface receptors and increases in the cytoplasmic concentration of cell signaling molecules such as PI3-kinase and MEK-ERK, which are involved in hESC maintenance (see, J. Li et al., MEK/ERK signaling contributes to the maintenance of human embryonic stem cell self-renewal, *Differentiation* 75 (2007), 299-307).

Recently, the Hubbell laboratory developed and tested various synthetic substrates for their capacity to maintain mouse ES cell self-renewal and concluded that simultaneous ligation of α5β1-, αvβ5-, α6β1, and α9β1 integrins promotes stemness of ES cells. These integrins have also been implicated in the regulation of mouse and human ES cell self-renewal in a number of other studies performed under various growth conditions (see, Sandhanakrishnan Cattavarayan et al., α6β1- and αv-integrins are required long-term self-renewal of murine embryonic stem cells in the absence of LIF, *BMC Cell Biology* 2015, 16:3; Y. Meng et al., Characterization of integrin engagement during defined human embryonic stem cell culture, *FASEB J.* 2010, 24(4): 1056-65; S. R. Braam et al., Recombinant vitronectin is a functionally defined substrate that supports human embryonic stem cell self-renewal via αvβ5 integrin, *Stem Cells* 2008; 26(9):2257-65).

Also provided is a microenvironmentally defined surface that activates α5β1, α6β1 and/or αvβ5 simultaneously or sequentially in order to regulate signaling pathway for self-renewal and pluripotency maintenance of a stem cell. Any suitable substrate protein containing peptide ligand to activate integrin α5β1-, αvβ5-, α6β1, or α9β1 simultaneously or sequentially to support self-renewal and pluripotency of a stem cell. In one embodiment, the microenvironment surface provides a substrate protein presenting α5β1 integrin activating motif or heparin binding motif derived from fibronectin domain III. Any suitable α5β1 integrin activating- or heparin binding motif can be selected from RGD (SEQ ID NO:15), GRGDSP (SEQ ID NO:16), PHSRN-RGDSP (SEQ ID NO:17), SPPRRARVT (SEQ ID NO:18), WQPPRARI (SEQ ID NO:19), KNNQKSEPLI-GRKKT (SEQ ID NO:20), or its combination of α5β1 integrin activating motif and heparin binding motif.

In another embodiment, the microenvironment surface provides a substrate protein presenting α6β1 integrin activating motif-derived laminin α1 or laminin α5 LG domain to support self-renewal and pluripotency of a stem cell. Any suitable α6β1 integrin activating motif can be selected from GKNTGDHFVLYM (SEQ ID NO:22), VVSLYN-FEQTFML (SEQ ID NO:23), RFDQELRLVSYN (SEQ ID NO:24), RLVSYSGVLFFLK (SEQ ID NO:25), ASKAI-QVFLLGG (SEQ ID NO:26), VLVRVERATVFS (SEQ ID NO:27), TVFSVDQDNMLE (SEQ ID NO:28), RLRGPQRVFDLH (SEQ ID NO:29), FDLHQNMGSVN (SEQ ID NO:30), QQNLGSVNVSTG (SEQ ID NO:31), SRATAQKVSRRS (SEQ ID NO:32), TWYKIAFQRNRK (SEQ ID NO:33), NRWHSIYITRFG (SEQ ID NO:34), RNIAEIIKDI (SEQ ID NO:51).

In another embodiment, the microenvironment surface provides a substrate protein presenting a combinatorial motif of α5β1 integrin activating motif and α6β1 binding motif at the same time to support self-renewal and pluripotency of a stem cell. Suitable combinatorial motif is a combination of PHSRN-RGDSP (SEQ ID NO:17) and NRWHSIYITRFG (SEQ ID NO:34) to support self-renewal and pluripotency of a stem cell.

Generally embryonic stem cells grow as individual colonies, maintained via E-cadherin-mediated cell-cell contact. Transcription profiling studies have revealed that over 60% of genes are expressed in ES cells (compared to only 10-20% in somatic cells) and most of these are involved in signal transduction and regulation, making ES cells very responsive to the microenvironment (see, C. E. Eckfeldt, E. M. Mendenhall, C. M. Verfaillie, The molecular repertoire of the "almighty" stem cell, Nat. Rev. Mol. Cell Biol. 2005, 6:726-737; N. Sato, I. M. Sanjuan, M. Heke, M. Uchida, F. Naef, A. H. Brivanlou, Molecular signature of human embryonic stem cells and its comparison with the mouse, Dev. Biol. 2003; 260:404-413).

Provided is a microenvironmentally defined surface that binds to cadherin to form colony for self-renewal and stemness maintenance in defined conditions. Any suitable cadherin binding motif can be selected from LFSHAVSSNG (SEQ ID NO:52), ADTPPV (SEQ ID NO:53), DQNDN (SEQ ID NO:54), or LRAHAVDING (SEQ ID NO:55).

Fibroblast growth factors (FGFs) are essential for maintaining self-renewal in human embryonic stem cells and induced pluripotent stem cells. Recombinant basic FGF (bFGF or FGF2) is conventionally used to culture pluripotent stem cells. Today FGF family consists of 23 members including acidic and basic fibroblast growth factor, and each FGF has canofin, hexfin, and decafin domain (S. Li et al., Fibroblast growth factor-derived peptides: functional agonists of the fibroblast growth factor receptor, J. Neurochem. 2008 February 104(3):667-82; S. Li et al., Agonists of fibroblast growth factor receptor induce neurite outgrowth and survival of cerebellar granule neurons, Dev. Neurobiol. 2009, 69(13):837-54; Li Shizhong et al., Neuritogenic and Neuroprotective Properties of Peptide Agonists of the Fibroblast Growth Factor Receptor, Int. J. Mol. Sci. 2010; 11(6): 2291-2305).

FGFRs are transmembrane glycoproteins with three extracellular domains, Ig1, Ig2 and Ig3. An FGFR fragment Ig2 and Ig3 is the minimal unit sufficient for specific ligand binding (see, V. I. Manfè et al., Peptides derived from specific interaction sites of the FGF 2-FGF receptor complexes induce receptor activation and signaling (see, J. Neurochem. 2010, 114(1):74-86; S. K. Olsen et al. (2004), Insights into the molecular basis for fibroblast growth factor receptor autoinhibition and ligand-binding promiscuity, Proc. Natl Acad. Sci. USA 101 935-940).

Bell et al. (see, 2000 Rotational coupling of the transmembrane and kinase domains of the Neu receptor tyrosine kinase, Mol. Biol. Cell 11:3589-3599) demonstrated that activation of receptor tyrosine kinases requires specific orientations of the kinase domains in a formed receptor dimer. The ligand binding mediates the optimal rotational positioning of the individual monomers within the dimer and thus the specific orientation of the catalytic domains. Binding of different agonists, such as FGF2 and canofins resulted in different modes of orientation of catalytic domains yielding differences in receptor activation (see, V. Manfe et al., Peptides derived from specific interaction sites of the fibroblast growth factor 2—FGF receptor complexes induce receptor activation and signaling, J. Neurochem. 2010, 114 (1):74-86).

When a growth factor binds to the extracellular domain of a receptor tyrosine kinase (RTK), its dimerization is triggered with other adjacent RTKs. Dimerization leads to a rapid activation of the protein's cytoplasmic kinase domains and the activated receptor as a result then becomes autophosphorylated on multiple specific intracellular tyrosine residues, resulting in signal transduction cascade.

Recent studies have demonstrated that the immobilization of soluble factors such as FGF, TGF or cytokines to the ECM plays an important role in mediating their biological effects (see, C. C. Rider (2006), Heparin/heparan sulphate binding in the TGF-beta cytokine superfamily, Biochem. Soc. Trans. 34:458-460). Presentation of soluble factors in an immobilized fashion alters their local effective concentration, bioavailability, and stability, and thereby modulates their effects on target cells. For example, NSC-proliferative regions in the SVZ are situated in proximity to regions, in which growth factors including basic fibroblast growth factor-2 are concentrated by heparan sulfate proteoglycan (HSPG) (see, F. Mercier et al. (2002), Anatomy of the brain neurogenic zones revisited: fractones and the fibroblast/macrophage network, J. Comp. Neurol. 451:170-188).

Provided is the FGF mimetic comprises recombinant mussel adhesive protein functionalized with FGF-derived peptide motif derived from hexafin domain or canofin domain. Preferably, FGF1 mimetic peptide motif can be selected from TGQYLAMDTDGLLYGS (SEQ ID NO:35), WFVGLKKNGSCKRG (SEQ ID NO:36), and FGF2 mimetic peptide motif can be selected from hexafin domain-derived ANRYLAMKEDGRLLAS (SEQ ID NO:37), ERGVVSIKGV (SEQ ID NO:38) or decafin domain-derived WYVALKRTGQYKLG (SEQ ID NO:39), canofin domain-derived HFKDPKRLYCK (SEQ ID NO:40), FLPMSAKS (SEQ ID NO:41), KTGPGQKAIL (SEQ ID NO:42), and FGF4 mimetic peptide motif can be selected from SRFFVAMSSKGKLYGS (SEQ ID NO:43), MFIAL-SKNGKTKKG (SEQ ID NO:44).

In one embodiment hereof, a microenvironment surface that combinatorially regulates the activity of both integrin and growth factor receptor to support self-renewal and pluripotency of murine embryonic stem cell is provided. The microenvironment surface comprises a substrate protein functionalized with a peptide such as fibronectin-derived peptide PHSRN-RGDSP (SEQ ID NO:17) to target α5β1 and FGF2-derived peptide selected from ANRYLAM-KEDGRLLAS (SEQ ID NO:37), ERGVVSIKGV (SEQ ID NO:38), WYVALKRTGQYKLG (SEQ ID NO:39), HFKDPKRLYCK (SEQ ID NO:40), FLPMSAKS (SEQ ID NO:41), KTGPGQKAIL (SEQ ID NO:42) to target FGF receptor; FGFR2IIIc.

Also provided is a microenvironment surface to activate TGF receptor to induce signaling pathway to activate transcriptional factors for self-renewal and pluripotency of pluripotent stem cell. A recombinant mussel adhesive protein as a substrate protein containing TGF mimetic peptide to bind to TGFβ receptor domain TβRI or TβRII can be used herein. Preferably, TGFβ mimetic peptide can be selected from LTGKNFPMFHRN (SEQ ID NO:43), MHRMPSFLPTTL (SEQ ID NO:46).

In one embodiment hereof, a microenvironment surface that combinatorially regulates the activity of both integrin and growth factor receptor to support self-renewal and pluripotency of an embryonic stem cell is provided. The microenvironment surface comprises a substrate protein presenting a combinatorial motif to activate α5β1 integrin and TGFβ receptor at the same time. The combinatorial motif is a combination of the substrate protein functionalized with a peptide such as fibronectin-derived peptide PHSRN-RGDSP (SEQ ID NO:17) to target α5β1 and TGFβ-derived peptide LTGKNFPMFHRN (SEQ ID NO:45), or MHRMPSFLPTTL (SEQ ID NO:46).

Provided is a microenvironment surface that generates WNT/β-catenin signaling pathway by presenting WNT 1 peptide motif LCCGRGHRTRTQRVTERCNC (SEQ ID NO:47) or LGTQGRLCNKTSEGMDGCEL (SEQ ID NO:48). In one embodiment hereof, provided is a microenvironment surface that combinatorially regulates the activity of both integrin and frizzled receptor to support self-renewal and pluripotency of an embryonic stem cell. The microenvironment surface comprises a substrate protein presenting a combinatorial motif to activate α5β1 integrin and frizzled receptor at the same time. The combinatorial motif is a combination of the substrate protein functionalized with a peptide such as fibronectin-derived peptide PHSRN-RGDSP (SEQ ID NO:17) to target α5β1 and WNT-derived peptide LCCGRGHRTRTQRVTERCNC (SEQ ID NO:39) or LGTQGRLCNKTSEGMDGCEL (SEQ ID NO:40).

Provided is a microenvironment surface that generating LIF/STAT3 signaling pathway by presenting LIF peptide motif IVPLLLLVLH (SEQ ID NO:49) or YTAQGEPFPNN-VEKLCAP (SEQ ID NO:50).

Various studies suggest that co-clustering or synergism occurs between downstream signaling molecules, once the basic requirements are met: growth factor receptor ligand-binding, integrin occupancy by a ligand and clustering of each type of receptor (see, M. A. Schwartz and V. Baron, Interactions between mitogenic stimuli, or, a thousand and one connections, *Curr. Opin. Cell Biol.* 11:197-202 (1999); K. M. Yamada and E. H. J. Danen, Integrin signaling, In *Signaling Networks and Cell Cycle Control* (ed. J. S. Gutkind) 1-25 (Humana Press, Totowa, N.J., 2000); S. Miyamoto et al., Integrins can collaborate with growth factors for phosphorylation of receptor tyrosine kinases and MAP kinase activation: roles of integrin aggregation and occupancy of receptors, *J. Cell Biol.* 135:1633-1642 (1996)).

Provided is a microenvironment surface to activate at least two different receptors simultaneously by presenting a substrate protein having combinatorial motifs comprising at least two different peptide motifs that bind to adhesion receptors such as integrin, co-receptors such as growth factor- or cytokine receptor, or combination thereof. The suitable combinatorial motifs may include one or more spacers between two peptide motifs to optimize flexibility and/or solubility and so afford increased affinity and/or bioavailability. The combinatorial motifs may have a peptide spacer sequence of at least two amino acids, preferably 2-15 amino acids, appended to the C-termini of at least one of the two peptide motifs.

A microenvironmentally defined 3D surface is provided. The 3D surface may be microenvironmentally defined over media found within a cell culture plate or other structure. A Substrate for the defined surface may include patterned or porous nanofiber being composed of various materials including polyvinylidene fluoride (PVDF), but not limited to cellulose, nylon, glass fiber; materials for bio-reactors used in batch or continuous cell culture or in bioreactors.

As used herein "nanofiber" refers to the electroprocessed composition that may include particles being larger than a nanofiber as a result of the electroprocessed composition, where the surface of the nanofiber presents biochemical cues. Collectively, the nanofiber may provide in vivo like microenvironment to regulate the fate of cells of interest.

As used herein, "WebTrix™" refers to a nanofibrous matrix to mimic three-dimensional microenvironment presenting biochemically defined and physically defined surface for precise regulation of cellular behavior such as cell adhesion, migration, growth, proliferation. WebTrix™ is the trade name for biochemically and physically defined nanofiber matrix and marketed by AMO LifeScience Co. Ltd.

Provided is a three-dimensional microenvironment comprised of a nanofiber sheet presenting a plurality of adhesion receptor binding peptide motifs derived from extracellular matrix (ECM) or cadherin and co-receptor binding peptide motifs derived from growth factor (GF) or cytokine that precisely regulate cellular behavior such as cell adhesion, migration, growth or differentiation. The nanofiber may include dispersed particles being at least partially embedded into the nanofibers as a result of electroprocessed composition, the particle being larger than the average diameter of nanofibers.

In one embodiment hereof, a combinatorial microenvironment surface comprising a nanofiber substrate having an average diameter of 100 nm to 20 microns, wherein the nanofiber surface presents extracellular components comprising extracellular matrix mimetic, growth factor mimetic, WNT mimetic, cytokine mimetic such as IL-3, LIF mimetic or combinations thereof.

Provided is an electroprocessable biofunctional composition to engineer an extracellular microenvironment presenting controlled physical and/or biochemical cues. As used herein "biofunctional composition" refers to a composition that comprises a bioactive component and a structural component that is electroprocessable polymer solution. Electroprocess including electrospinning or electro-spraying is a means of producing fibers or particles with diameters generally between 10 to 2,000 nanometers. It has the ability to produce fibers or particles that are far smaller than those produced by conventional means such as wet spinning or melt spinning.

Bioactive component is a, natural or synthetic, polymer or protein containing peptide motif. As used herein "peptide motif" refers to a short peptide, preferably three (3) to one hundred (100) amino acids in length that possesses a peptide derived from natural protein such as extracellular matrix (ECM), growth factors (GFs), or cytokines that mimic natural ECM, GF, or cytokine activity. Preferably, the bioactive peptide is a peptide that was originally identified in nature, produced by an animal, plant, fungus or bacterium as part of their natural mechanism.

Provided is an electrospinnable biofunctional composition for a fibrous extracellular microenvironment comprised of two components, extracellular component and, and a structural component. In one embodiment, a structural component is a polymer to provide physical or mechanical cues such as pore size or elasticity whereas extracellular component provides biochemical cues.

Any electrospinnable polymer, natural or synthetic, for use in this disclosure can be a structural component. Preferably, an electrospinnable polymer is a synthetic polymer which has the appropriate viscosity in solution. Any polymer meeting the above requirements is useful herein, and the selection of the specific polymer and acquisitions or preparation of such polymer would be conventionally practiced in the art (see, reference here). Preferred for such electrospinnable polymers are selected from groups comprising polyvinylidene fluoride (PVDF), polyacrylonitrile (PAN), polyethersulfone (PES), polylactic acid (PLA), polyglycolic acid (PGA), poly (lactide-glycolic) acid (PLGA), polycaprolactone, poly(alkylene oxides) particularly poly(ethylene glycols), poly(vinyl alcohols), polypeptides, poly(amino acids), such as poly(lysine), poly(allylamines) (PAM), poly (acrylates), polyesters, polyphosphazenes, pluronic polyols, polyoxamers, poly(uronic acids), and copolymers, including graft polymers thereof.

This disclosure can be used in high throughput screening (HTS) to identify combinatorial peptide motifs to engineer optimal synthetic microenvironment that can specifically, selectively, simultaneously or sequentially generate signaling pathway to regulate self-renewal and pluripotency of pluripotent stem cells.

A "microenvironment array" is a combination of two or more chambers. Preferably, an array is comprised of chambers in addressable rows and columns. The layout of microenvironment arrays produced according to the disclosure can vary, dependent upon the particular cell lines of interest, for example, induced pluripotent stem cell or embryonic stem cell.

A method for providing for a device of microenvironment array comprises:
(a) preparing a biochemical cue composition;
(b) placing the composition on the surface of a substrate for coating; and
(c) obtaining the extracellular microenvironment array.

In one embodiment hereof, a microenvironment array is provided. The array is a 12-well, microwell plate consisting of 4×3-well. Each well within a strip (4 wells total) is pre-coated with a different biofunctional composition to generate different extracellular microenvironment. Cells of interest can be seeded onto each well, whereby cells are cultured on different extracellular microenvironment surface. An extracellular microenvironment that induces a desirable cellular behavior can be identified and designed from the assay utilizing this extracellular microenvironment array.

Provided is an antimicrobial environment where biological contamination is sufficiently prohibited without use of antibiotics. Microbial contamination is a major issue in cell culture, but there are a range of procedures which can be adopted to prevent or eliminate contamination. Contamination may arise from the operator and the laboratory environment, from other cells used in the laboratory, and from reagents. Antimicrobial surface can prevent this kind of microbial contamination by presenting antimicrobial peptide acting only on microbial membrane surface but not mammalian cytoplasmic membrane. The antimicrobial surface comprises mussel adhesive protein as a substrate protein, functionalized with one or two antimicrobial peptides which can be recombinantly incorporated into C-, N terminus or both C- and N-terminus of the substrate protein. The antimicrobial peptide can be selected from KLWKK-WAKKWLKLWKA (SEQ ID NO:59), FALALKALKKL (SEQ ID NO:60), ILRWPWWPWRRK (SEQ ID NO:61), AKRHHGYKRKFH (SEQ ID NO:62), KWKLFKKI-GAVLKVL (SEQ ID NO:63), LVKLVAGIKKFLKWK (SEQ ID NO:64), WSILAPLGTTLVKLVAGIGQQKRK (SEQ ID NO:65), GIGAVLKVLTTGLPALISWI (SEQ ID NO:66), SWLSKTAKKGAVLKVL (SEQ ID NO:67), KKLFKKILKYL (SEQ ID NO:68), GLKKLISWIKRAAQQG (SEQ ID NO:69), and GWLK-KIGKKIERVGQHTRDATIQGLGIAQQAANVAATAR (SEQ ID NO:70).

In one embodiment, antimicrobial nanofibrous surface was provided to inhibit bacterial growth and facilitate growth and proliferation of cells of interest.

The following examples are provided to demonstrate preferred embodiments hereof and the disclosure is not intended to be limited in scope by the specific embodiments described herein, which are intended for the purposes of exemplification only. Functionally equivalent products, compositions and methods are clearly within the scope of the disclosure, as described herein.

EXAMPLES

Example 1

Preparation of Electrospinnable Biofunctional Composition to Engineer an Extracellular Microenvironment PVDF with an average molecular weight of 200 kDa from Sigma Aldrich (St. Louis, USA), PAN with an average molecular weight of 200 kDa, PES with an average molecular weight of 200 kDa purchased from Sigma Aldrich (St. Louis, USA), PLA with an average molecular weight of 200 kDa purchased from Sigma Aldrich were dissolved in DMAc to prepare 20 wt % solution. MAPTrix™ ECM (no peptide motif, PHSRN-RGDSP (SEQ ID NO:17) (combo) containing, and RGD motif containing) purchased from Kollodis BioSciences (North Augusta, S.C., USA) was dissolved in an aqueous solution composed of distilled water and DMAc. Each polymer solution was mixed well together with MAPTrix™ ECM solution by vortexing it for 10 minutes to make homogeneous 18 wt % solution.

The electrospinnable (e-spin) solution was placed in a plastic syringe fitted with a 27 G needle. A syringe pump (KD Scientific, USA) was used to feed the e-spin solution into the needle tip. A high voltage power supply was used to charge the needle tip. The nanofibers were collected onto grounded aluminum foil target located at a certain distance from the needle tip. The fiber meshes were then removed, placed in a vacuum chamber for two days to remove residual solvent, and then stored in a desiccator. Silver staining was used to detect MAPTrix™ protein on the surface of nanofiber membrane.

FIG. 1 shows a comparison of the nanofiber sheet of PVDF with those of PVDF blended with MAPTrix™. The PVDF nanofiber sheet was not stained while brown colored area was observed in the blended PVDF nanofiber sheet, regardless of the type of MAPTrix™ ECM protein, indicating that the hydrophilic protein MAPTrix™ surfaced on the nanofiber sheet during the electrospinning. Therefore, hydrophilic MAPTrix™ homogeneously and stably dispersed in the hydrophobic PVDF solution could be electrospun to biologically functionalize the PVDF nanofiber surface that supports cell attachment, migration, growth, and proliferation.

The electrospinnable composition and electrospinning conditions are summarized in Tables 1 and 2, respectively.

TABLE 1

Electrospinnable solution composition (structural component)

| Polymer | Solvent | MAPTrix ™ | Solvent (1 mL) |
|---|---|---|---|
| PVDF 100 mg | DMAc 5 mL | 7 mg | DW/DMAc (0.1/0.9) |
| PES 100 mg | DMAc 5 mL | 7 mg | DW/DMAc (0.1/0.9) |
| PAN 100 mg | DMAc 5 mL | 7 mg | DW/DMAc (0.1/0.9) |
| PLGA 100 mg | DMAc 5 mL | 7 mg | DW/DMAc (0.1/0.9) |
| PVDF/PAN 50 mg/50 mg | DMAc 5 mL | 7 mg | DW/DMAc (0.1/0.9) |
| PVDF/PES 50 mg/50 mg | DMAc 5 mL | 7 mg | DW/DMAc (0.1/0.9) |

TABLE 2

Electrospinning Parameters

| E-Solution | Concentration | Voltage (kv) | Rate (mL/min) | Distance (cm) |
|---|---|---|---|---|
| PVDF | 18% | 21 | 0.1 | 11 |
| PES | 18% | 21 | 0.1 | 10 |
| PAN | 18% | 21 | 0.1 | 10 |
| PLGA | 18% | 21 | 0.1 | 11 |
| PVDF/PAN | 18% | 21 | 0.1 | 10 |
| PVDF/PS | 18% | 21 | 0.1 | 10 |

E-solution is the electrospinnable biofunctional composition prepared from the procedure described above in EXAMPLE 1.

The nanofiber membranes obtained were stained.

Example 2

Preparation of Nanofiber Having Different Diameter

Each Polyvinylidene fluoride (PVdF)-Kynar 761(Homopolymer, Mw: 400,000-500,000), and Polyvinylidene fluoride (PVdF)-Solef 21216(Co-polymer, Mw: 600,000) or Polyacrylonitril-Pulver (Co-PAN, Mw: 85,000) was dissolved in DMAC and blended. The blending ration of homopolymer to copolymer were 1:1, 1:2, 1:3, 1:4, 1:5, 1:6, 1:7, 1:8, 1:9. Nanofibers having different diameter were formed by the same procedure mentioned in EXAMPLE 1.

Figure 2A:
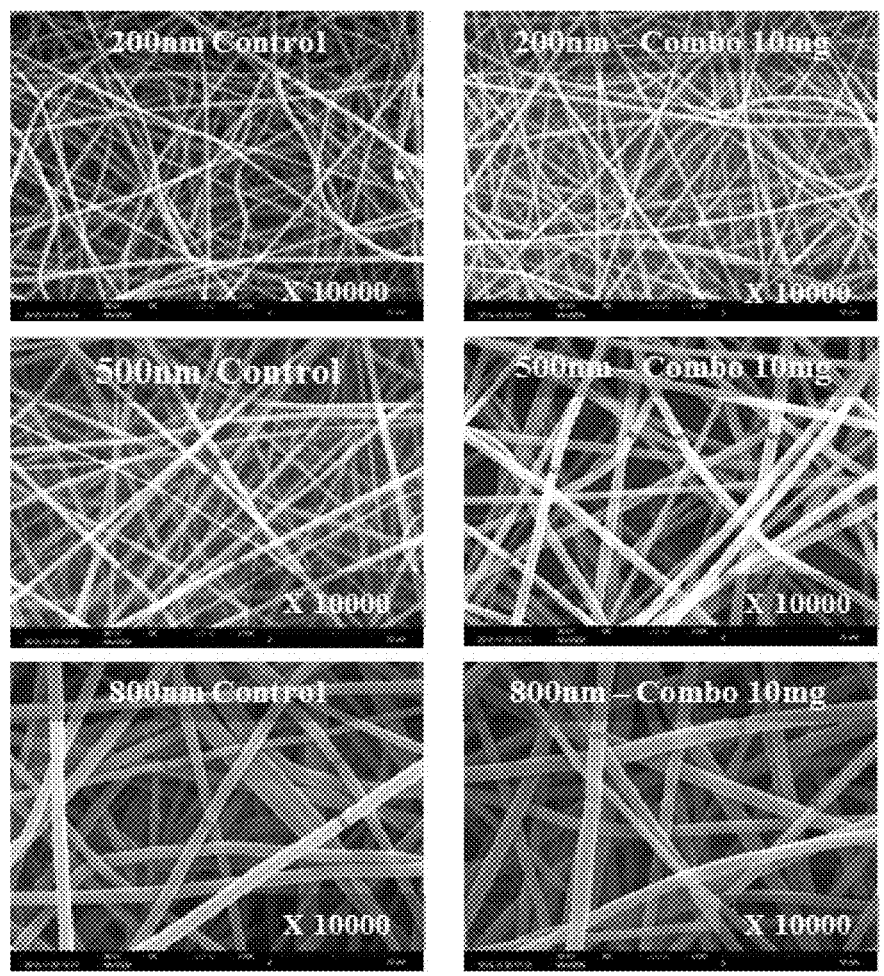
FIGS. 2A and 2B represent a synthetic nanofibrous microenvironment formed by electrospinning biofunctional composition. A combinatorial presentation of various peptide motifs immobilized on the nanofiber surface provides biochemical cues were surfaced on nanofibrous substrate.
Figure 2B:
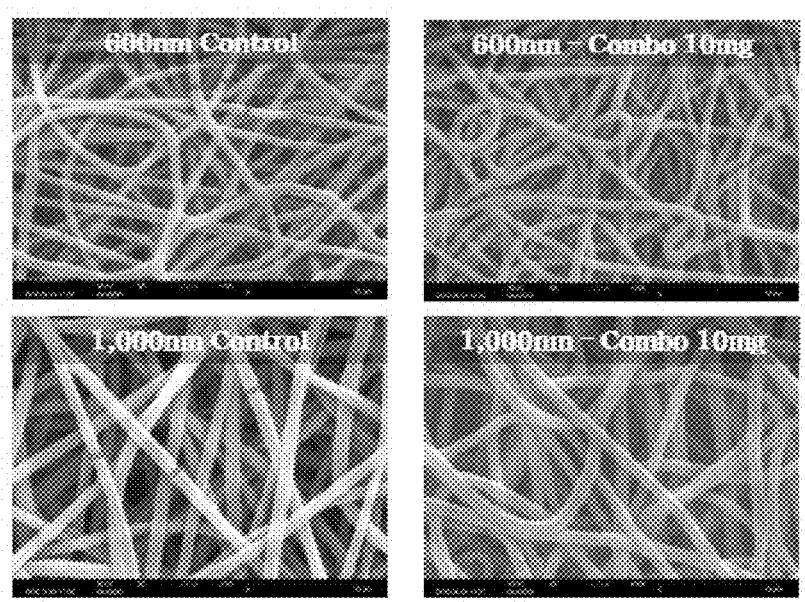

The diameter of each nanofiber sheet is measured by observation using a scanning electron microscope (SEM), a thin gold layer was deposited on the surface of each nanofiber sheet. FIG. 2A shows nanofiber sheets having a diameter of 200, 500, and 800 nm, respectively. FIG. 2B shows nanofiber sheets having a diameter of 600 and 1,000 nm, respectively.

Example 3

Preparation of Nanofiber Having Particles

MAPTrix™ ECM based particles were formed by reaction of the carboxyl group of MAPTrix™ activated by 1-ethyl-3-(3-dimethylaminopropyl) carbodiimides/N-hydroxysulfosuccinimide (EDC/s-NHS) on the C-terminus with the amino groups of the MAPTrix™.

1-Ethyl-3-[3-Dimethylaminopropyl]carbodiimide hydrochloride (EDC) solution is prepared by dissolving 10 mg of EDC in 1 ml of sodium bicarbonate buffer (10 mM, pH 6.5). 5 mg of solid sulfo-N-hydroxysulfosuccinimide (S—NHS) is added to the EDC solution. The EDC/S—NHS solution is added to the nanofiber surface to activate carboxyl group of MAPTrix™ surfaced on the nanofiber sheet for 30 minutes. After the C-terminus activation, 0.1 mg of MAPTrix™ having PHSRN-RGDSP (SEQ ID NO:17) motif dissolved in 1 mL distilled water was added to the nanofiber surface. Crosslinking is carried out at ambient temperature for 30 minutes to get crosslinked MAPTrix™ particle presenting PHSRN-RGDSP (SEQ ID NO:17) on the nanofiber surface.

Figure 3:
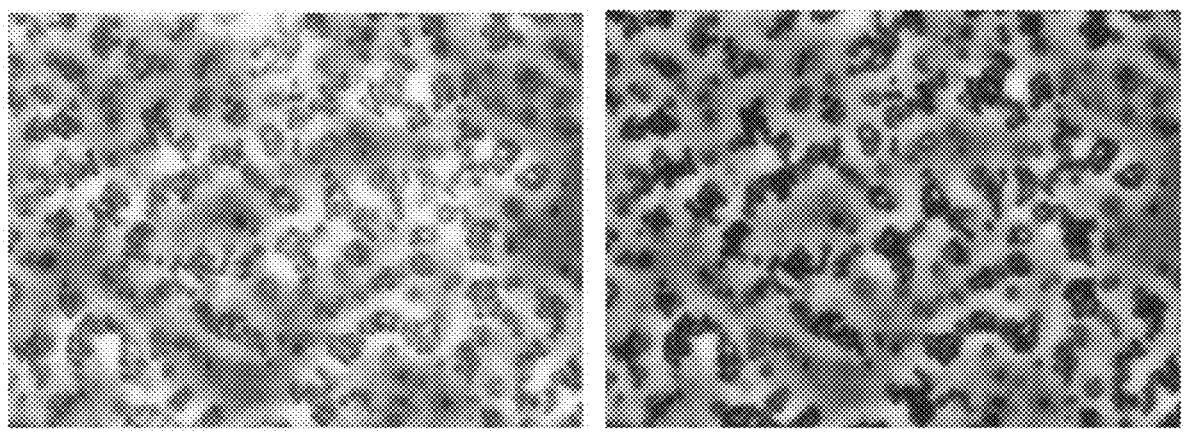
FIG. 3 represents nanofiber having MAPTrix particles whose size is about 5 μm. Various peptide motif can be presented on the particle surface in order to control the fate of various cells including stem cell.

As presented in FIG. 3, the MAPTrix™ particles were observed. Depending on the concentration of MAPTrix™, the particle size ranged from 0.5 to 5 μm.

Example 4

Cell Adhesion and Self-Renewal Assay

Cell fate is regulated by soluble factors such as FGFs and interactions involving cell-cell and cell-extracellular matrix (ECM) contacts. For example, cell survival or self-renewal of stem cells is required for cells to be anchored in their native microenvironment via cell adhesion molecules. Integrins are cell surface receptors that mediate cell-ECM contacts. The extracellular domains of integrins bind directly to ECM proteins such as collagen, fibronectin, and laminin. Many cells including pluripotent stem cells highly express several integrins including α5β1, α6β1, αvβ3.

Figure 4A:
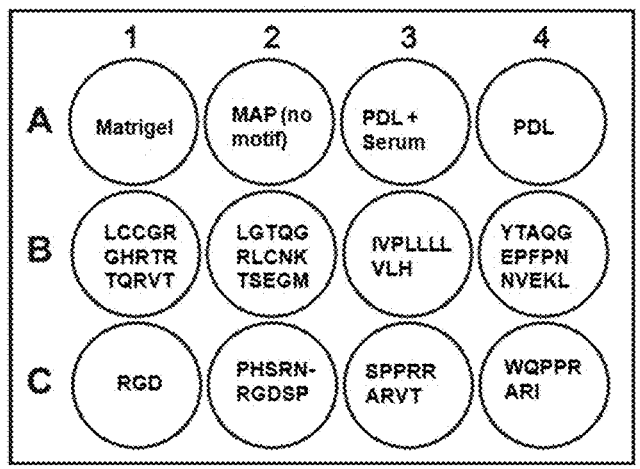
FIGS. 4A-4C represent the layout of synthetic microenvironment to screen an optimal extracellular microenvironment. The surface of each well presents integrin binding motif.
Figure 4B:
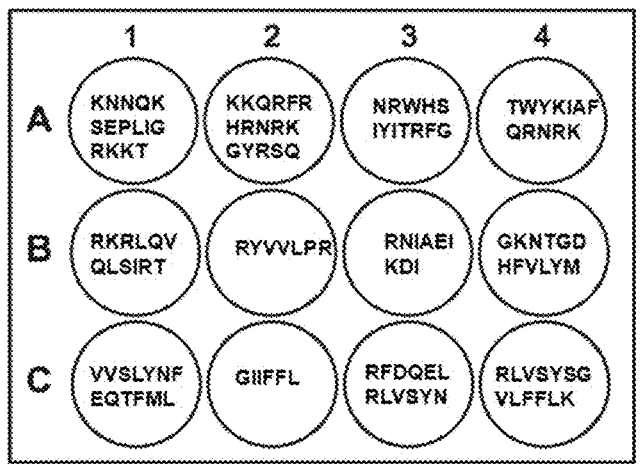
Figure 4C:
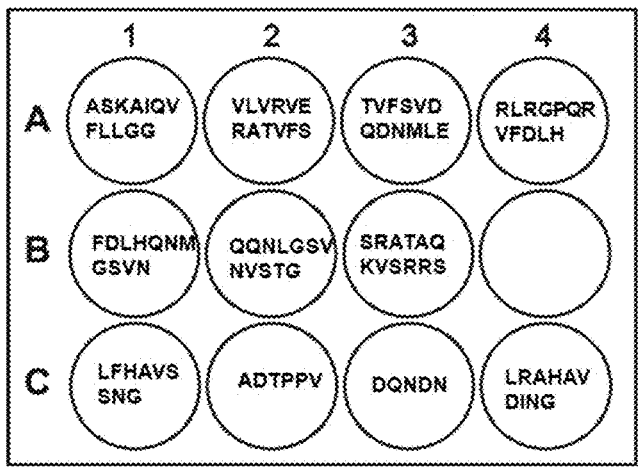

In order to identify peptide motifs that activate these integrins, arrays of 31 different peptide motifs that support cell-ECM interaction were prepared as represented in FIGS. 4A, 4B and 4C. A representative array surface to present fibronectin-derived peptide motif to bind integrin and was screened to identify cell-ECM interaction that supports self-renewal and pluripotency of murine embryonic stem cell.

For arraying, stock solutions of each ECM and cytokine such as WNT and LIF (leukemia inhibitory factor) mimetic were suspended and dissolved in distilled water at a concentration of 0.06 mg/mL. ECM and/or cytokine mimetic solutions were then coated in a 12 microwell plate via EDC/S—NHS mediated crosslinking reaction as set forth in EXAMPLE 3. The layout for each array was represented in FIGS. 4A, 4B and 4C, respectively.

For array preparation, the following MAPTrix™ were used for cell adhesion surface in each well.

TABLE 3

Peptide motif sequence

| Peptide motif | SEQ ID NO: | Source |
|---|---|---|
| RGD | 15 | Fibronectin |
| PHSRN-RGDSP | 17 | Fibronectin |
| SPPRRARVT | 18 | Fibronectin |
| WQPPRARI | 19 | Fibronectin |
| KNNQKSEPLLIGRKKT | 20 | Fibronectin |
| KKQRFRHRNRKGYRSG | 56 | Vitronectin |
| NRWHSIYITRFG | 34 | Laminin |
| TWYKIAFQRNRK | 33 | Laminin |
| RKRLQVQLSIRT | 21 | Laminin |
| RYVVLPR | 57 | Laminin |
| RNIAEIKDI | 51 | Laminin |
| GKNTGDHFVLYM | 22 | Laminin |
| VVSLYNFEQTFML | 23 | Laminin |
| GIIFFL | 58 | Laminin |
| RFDQELRLVSYN | 24 | Laminin |
| RLVSYSGVLFFLK | 25 | Laminin |
| ASKAIQVFLLGG | 26 | Laminin |
| VLVRVERATVFS | 27 | Laminin |
| TVFSVDQDNMLE | 28 | Laminin |
| RLRGPQRVFDLH | 29 | Laminin |
| FDLHQNMGSVN | 30 | Laminin |
| QQNLGSVNVSTG | 31 | Laminin |
| SRATAQKVSRRS | 32 | Laminin |
| LCCGRGHRTRTQRVTERCNC | 47 | WNT5 |
| LGTQGRLCNKTSEGMDGCEL | 48 | WNT1 |
| IVPLLLLVLH | 49 | LIF 1 |
| YTAQGEPFPNNVEKLCAP | 50 | LIF 2 |
| LFSHAVSSNG | 52 | E-cadherin |
| ADTPPV | 53 | E-cadherin |
| DQNDN | 54 | E-cadherin |
| LRAHAVDING | 55 | E-cadherin |

Example 5

Culture and Self-Renewal of ESCs on Adhesion Surface

The ability of integrin- or cytokine receptor activating surface to support self-renewal of mESCs was evaluated by serial passaging of murine ES cells on the microenvironment surface as prepared in EXAMPLE 4. These murine ES cells were obtained from cultures of early blastocysts. The array was incubated with media containing serum replacement media and murine embryonic stem cells were grown on the array for 5 days. For the maintenance of murine embryonic stem cell cultured on poly-D-lysine (PDL, Sigma-Aldrich) coated surface, DMEM Glutamax (GIBCO, Life Technology) containing high glucose 4.5 g/L, Na-pyruvate (0.11 g/L) and L-glutamine was used with 1% non-essential amino acid (Sigma-Aldrich), 50 U/mL Penicillin/streptomycin (GIBCO) and 0.1 mM 2-Mercaptoethanol (GIBCO) as the basal medium, which was added with 20% fetal bovine serum (FBS, Hyclone) and leukemia inhibitory factor (LIF, 1,000 units/mL, Millipore) at 37° C., 5% CO2 incubator.

The mESCs was cultured in KnockOut™ DMEM medium (Invitrogen) supplemented with 20% KnockOut™ Serum Replacement (KSR; Invitrogen), 0.1 mM of 2-mercaptoethanol (Invitrogen), MEM Non-essential Amino Acids (Invitrogen), GlutaMAX™ Supplement (Invitrogen), leukemia inhibitory factor (LIF, 1,000 units/mL, Millipore), and 60 ng/mL of MAPTrix™ PHSRN-RGDSP (SEQ ID NO:17) (Kollodis BioSciences).

Figure 5A:
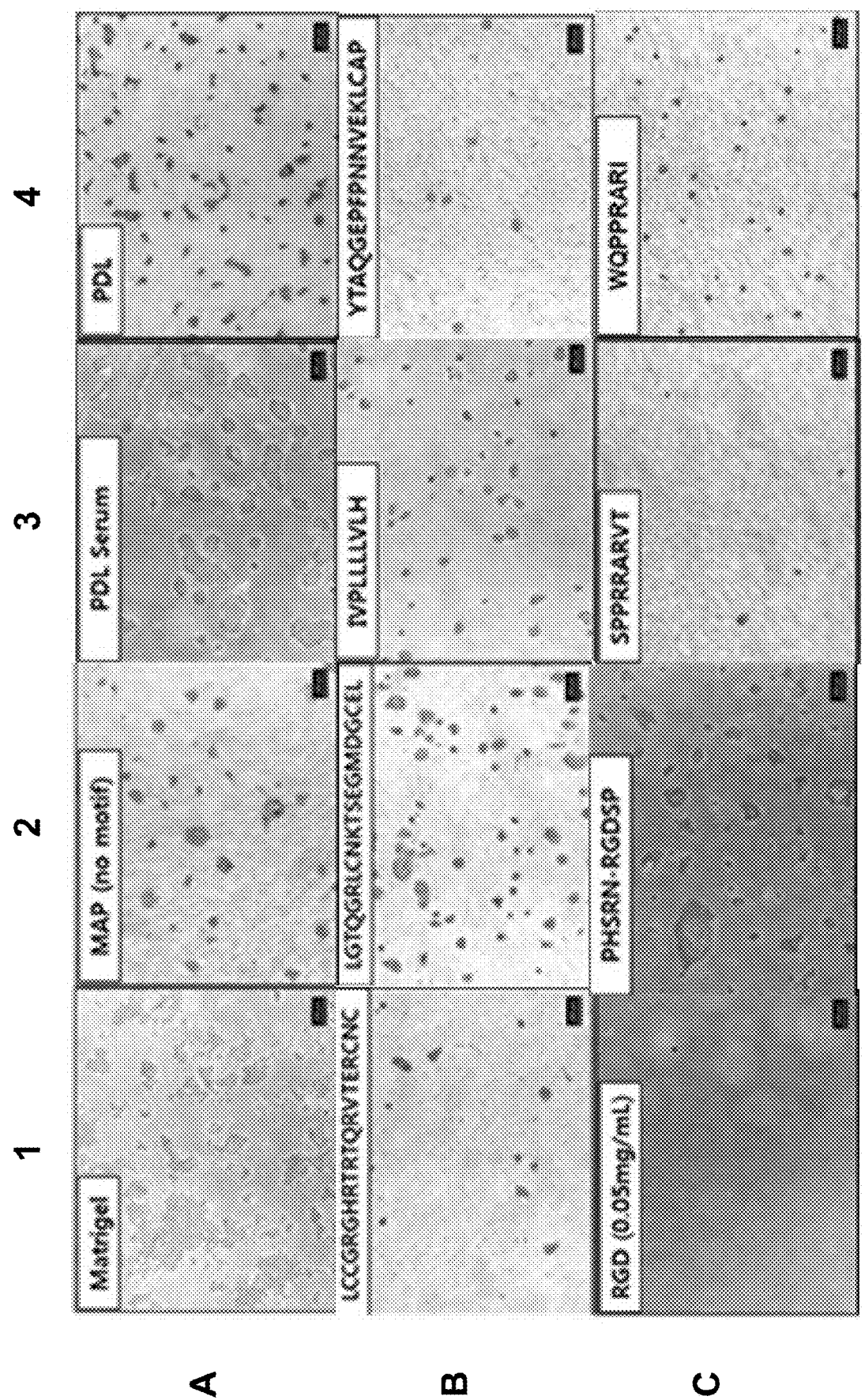
FIGS. 5A-5C represent the colony attachment of murine embryonic stem cells (mESC) seeded on various substrates.
Figure 5B:
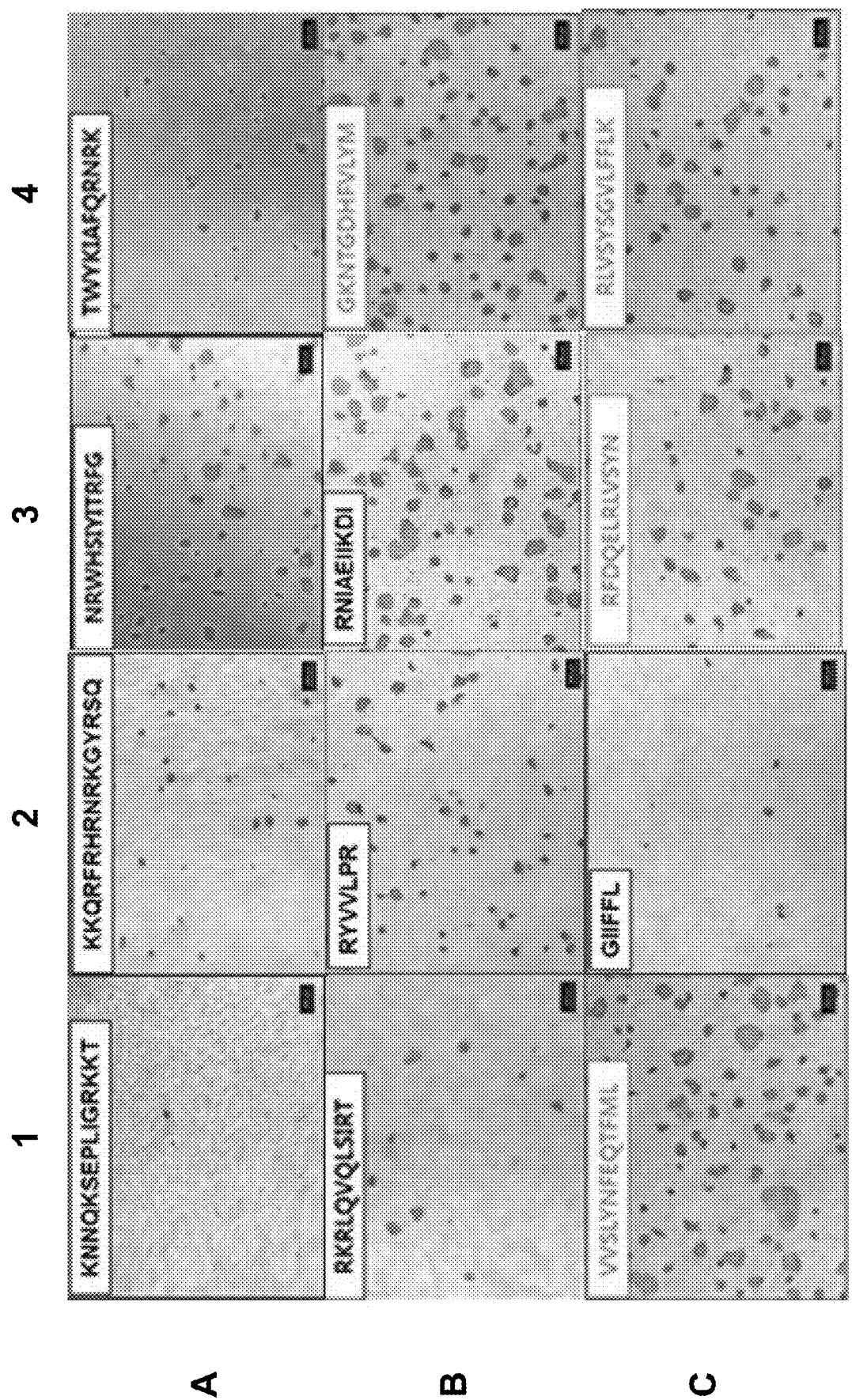
Figure 5C:
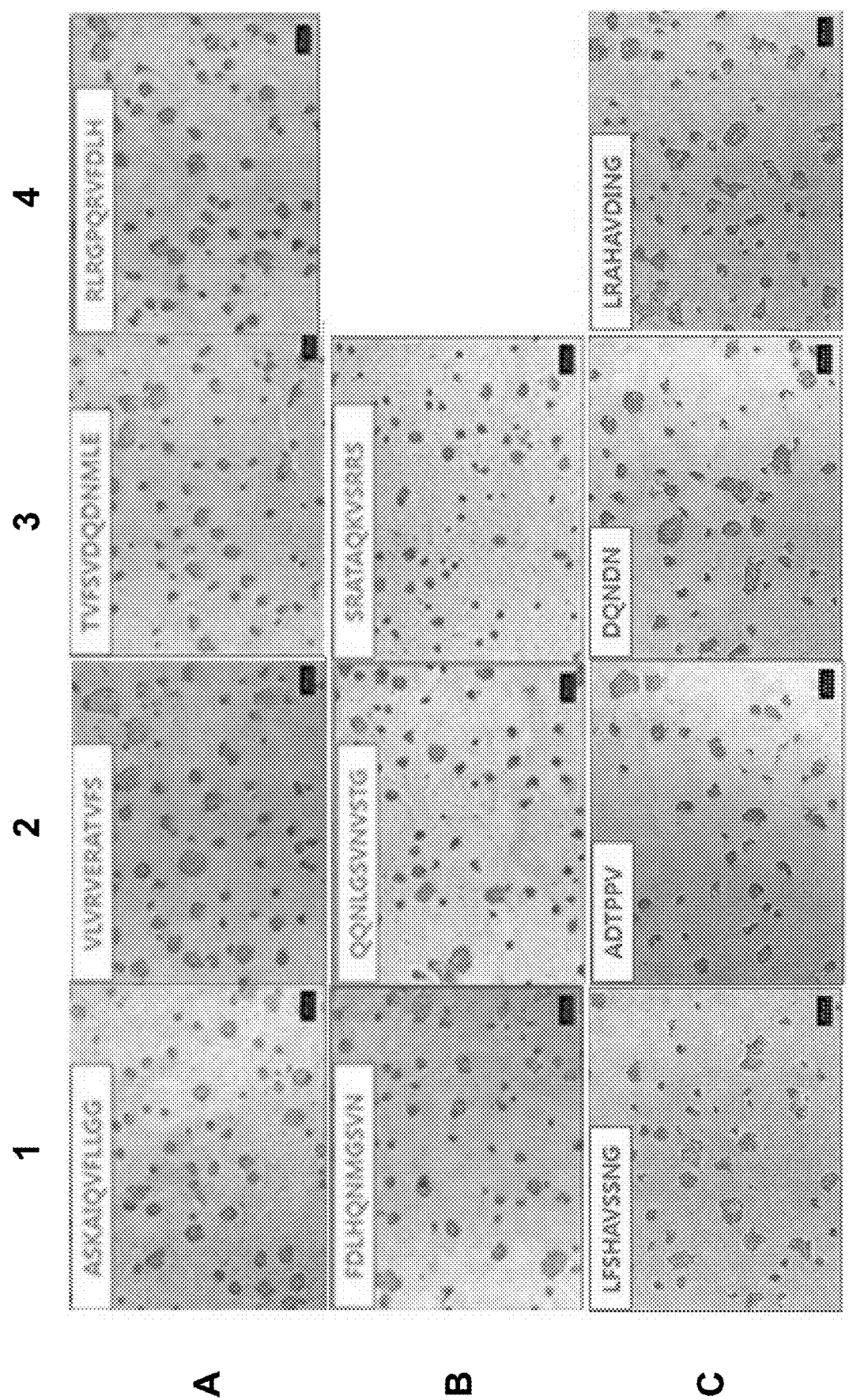

Cells were washed in PBS and fixed in formaldehyde (37%) for 30 seconds, washed and stained for 15 minutes in 100 µL of FBB Alkaline solution (Sigma-Aldrich) in sodium nitrile solution. Stained cells were analyzed on an Olympus microscope. FIGS. 5A, 5B and 5C show the murine stem cell cultured on the microenvironment surface presenting integrin-, cadherin-, or cytokine receptor binding motif were strongly stained with AP, indicating self-renewal without loss of its differential potential while the stem cells cultured on PDL-coated surface indicated the differentiated state.

We confirmed that the murine embryonic stem cells were maintained in an undifferentiated stage on the surface presenting several integrin-, cadherin-, and cytokine receptor binding peptide motifs as shown in FIG. 5. Particularly, fibronectin-derived motif PHSRN-RGDSP (SEQ ID NO:17), laminin-derived motif RNIAEIIKDI (SEQ ID NO:51), VVSLYNFEQTFML (SEQ ID NO:23), E-cadherin motif LFSHAVSSNG (SEQ ID NO:52) and DQNDN (SEQ ID NO:54), WNT-derived motif LGTQGRLCNKTSEGMDGCEL (SEQ ID NO:48) showed comparable self-renewal and growth of mESC with those of cells in serum conditions (PDL serum), but less comparable than those of cells cultured on Matrigel™ in terms of colony size and morphology.

Example 6

Concentration Effect of Fibronectin Mimetic on Self-Renewal

Among the peptide motifs identified in Example 5, α5β1 integrin binding motif PHSRN-RGDSP (SEQ ID NO:17) enabled mESCs to self-renewal and proliferate in an undifferentiated, comparable with those cultured on Matrigel™. To evaluate the concentration effect of PHSRN-RGDSP (SEQ ID NO:17) on human induced pluripotent stem cells (hiPS), the concentration effect of MAPTrix™ (PHSRN-RGDSP (SEQ ID NO:17) motif containing) on cell morphology, colony size and shape was analyzed. A wide range of concentration of MAPTrix™ coating solution was prepared and coated on the substrate according to the procedure as set forth in Example 4. The hiPS cells were cultured on the microenvironment surface prepared from the 0.01 mg/mL, 0.06 mg/mL, 0.1 mg/mL, 0.5 mg/mL, and 1 mg/mL coating solution.

Figure 6:
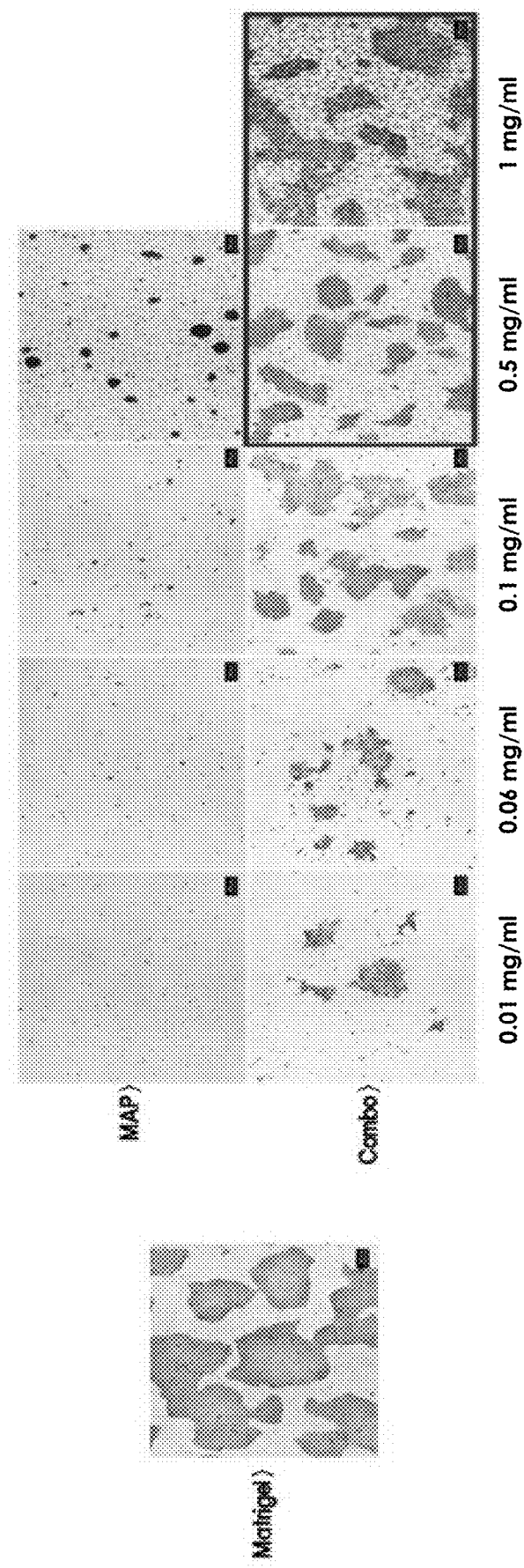
FIG. 6 represents the effect of integrin α5β1 binding motif (PHSRN-RGDSP (SEQ ID NO:17)) on the self-renewal and proliferation of human induced pluripotent stem cells. High density of α5β1 binding motif provided the favorable microenvironment to support self-renewal and proliferation of stem cells, comparable results with Matrigel™, while colony-of-partially-differentiated stem cells observed on the surface prepared from the concentration lower than 0.1 mg/ml.

FIG. 6 represents the concentration effect of PHSRN-RGDSP (SEQ ID NO:17) on self-renewal of human induced stem cells. AP staining indicated higher surface density of PHSRN-RGDSP (SEQ ID NO:17) motif, the bigger colony size and the better colony shape, significantly comparable with the cells cultured on Matrigel™.

Example 7

Microenvironment Surface Presenting Combinatorial Signaling from Crosstalk Between Integrin-Growth Factor Receptor FGF signaling appears to be of central importance to human pluripotent stem cells self-renewal. To evaluate the synergic effect of FGF signaling together with integrin signaling, a microenvironment surface presenting α5β1 integrin binding motif and FGF and TGFβ receptor binding motif was prepared in accordance with the procedure as set forth in Example 4. The concentration of MAPTrix™ containing FGF mimetic peptide ANRYLAMKEDGRLLAS (SEQ ID NO:37), ERGVVSIKGV (SEQ ID NO:38), WYVALKRTGQYKLG (SEQ ID NO:39), HFKDPKRLYCK (SEQ ID NO:40), FLPMSAKS (SEQ ID NO:41), KTGPGQKAIL (SEQ ID NO:42), and TGFβ mimetic peptide LTGKNFPMFHRN (SEQ ID NO:43), MHRMPSFLPTTL (SEQ ID NO:46) used to create microenvironment was 50 ng/mL. The concentration of MAPTrix™ containing PHSRN-RGDSP (SEQ ID NO:17) α5β1 integrin binding motif was 0.5 mg/mL. In contrast to the microenvironment surface, the same MAPTrix™ containing FGF mimetic peptide and TGFβ mimetic peptide solution were added to E6 medium in order to evaluate the MAPTrix™ FGF or TGFβ mimetic as supplements.

Human embryonic stem cells (H9) were maintained in serum replacement media conditions before switching from the serum-free media to the microenvironment surface. The cell clusters were seeded on the microenvironment surface in E6, E8, E6 supplemented with basic FGF (60 nM), E6 supplemented with TGFβ (5 nM), respectively. Medium was changed daily. After four days, cells were washed and fixed for AP staining according to the procedure as set forth in EXAMPLE 5.

Figure 7A:
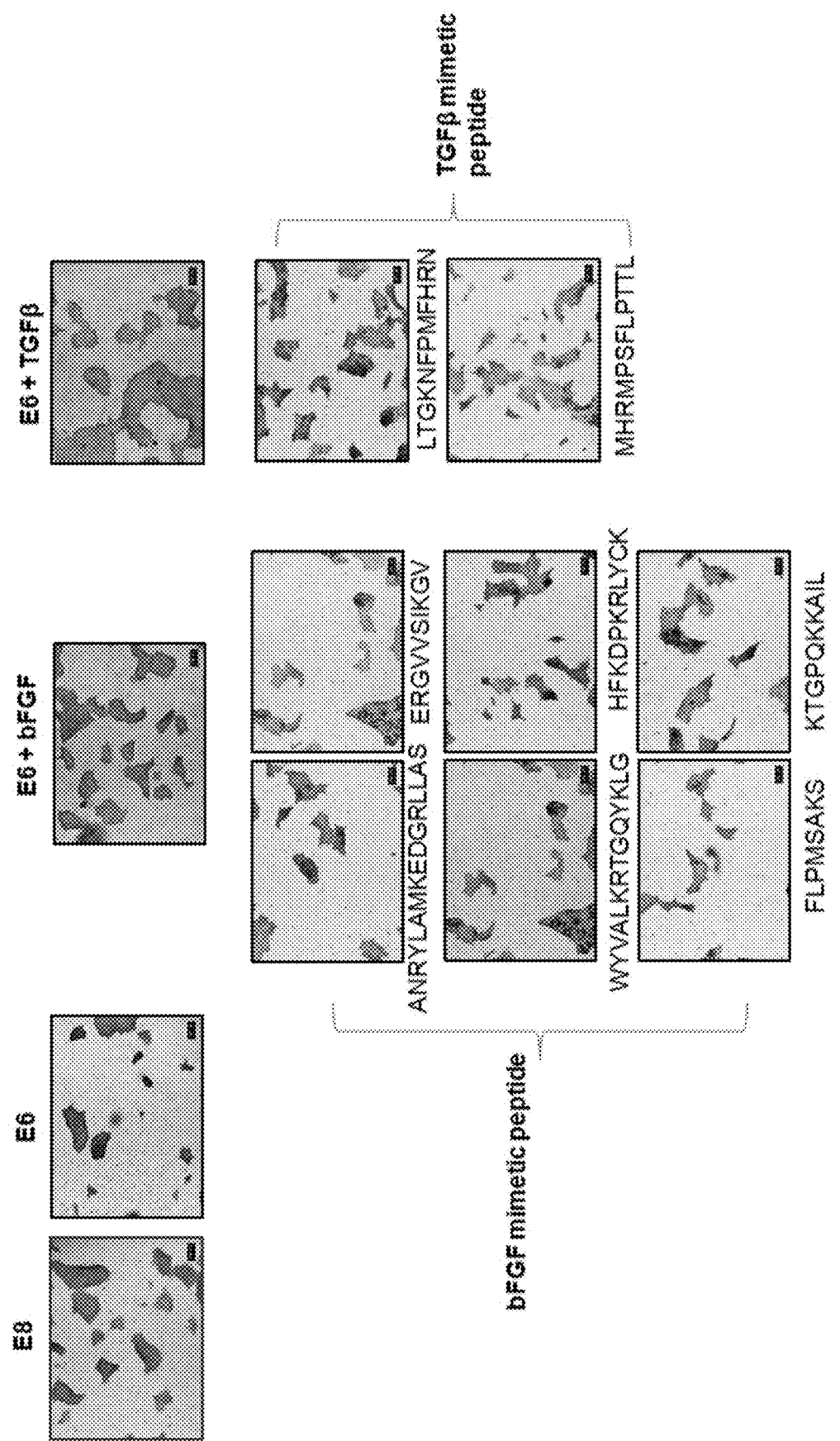
FIGS. 7A and 7B represent the effect of combinatorial signaling via crosstalk between integrin-FGF receptor signaling and integrin-TGFβ receptor signaling when FGF- and TGFβ mimetic peptide were added in the media solution and immobilized on the surface, respectively.
Figure 7B:
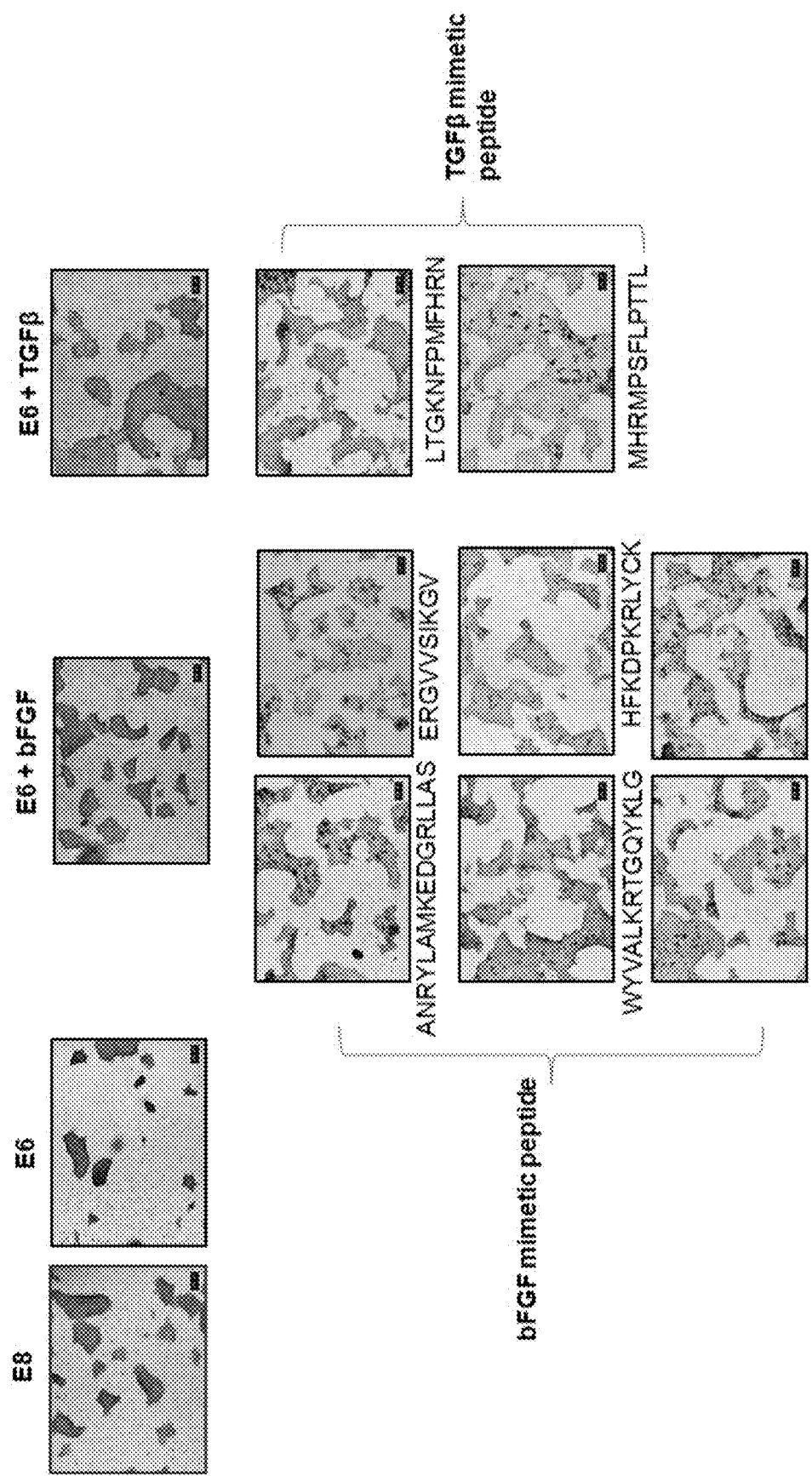

FIG. 7 represented the effect of combinatorial signaling via crosstalk between integrin and FGF receptor signaling and integrin-TGFβ receptor signaling. FIG. 7A represented the colony size and shape from MAPTrix™ FGF2 and TGFβ mimetic peptide containing media, and FIG. 7B represented the colony size and shape cultured on the microenvironment surface presenting α5β1 integrin binding motif PHSRN-RGDSP (SEQ ID NO:17), and individual FGF2 and TGFβ receptor binding motif. The colony cultured on the microenvironment surface was bigger and better (more undifferentiated state) than that on the MAPTrix™ FGF2 and TGFβ mimetic peptide containing media. Interestingly, the microenvironment surface from α5β1 integrin binding PHSRN-RGDSP (SEQ ID NO:17) and, FGF mimetic peptide ANRYLAMKEDGRLLAS (SEQ ID NO:37), WYVALKRTGQYKLG (SEQ ID NO:39), and TGFβ mimetic peptide MHRMPSFLPTTL (SEQ ID NO:46) showed bigger colony size compared to E6 supplemented with FGF2 or TGFβ, respectively, indicating combinatorial presentation of peptide motif may be more efficient than the combination of whole proteins of fibronectin and growth factors for self-renewal and proliferation of stem cells even though partially differentiated cells were observed on the microenvironment surface presenting the combinatorial signaling.

Example 8

Microenvironment Surface Presenting Combinatorial Signaling from Crosstalk Between Integrin and Growth Factor/Cytokine Receptor WNT signaling has been involved in the control over various types of stem cells including pluripotent stem cells and may act as a niche factor to maintain stem cells in a undifferentiated state. Addition of WNT mimetic peptide to the microenvironment surface may inhibit human embryonic stem cell (H9) from partially differentiation during the proliferation as shown in EXAMPLE 7.

A microenvironment surface to inhibit the partial differentiation was prepared by combining integrin-, growth factor receptor- and frizzled receptor binding motif. Two types substrate to create a microenvironment surface, namely, two-dimensional (2D) and three-dimensional (3D) substrate, but each has the same biochemical surface to induce the same combinatorial signaling.

A series of WebTrix™ matrices, 3D nanofibrous substrates, was prepared according to the procedure as set forth in EXAMPLE 1. Six-well plates from Thermo Fischer Scientific were used as 2D substrate. The composition to create combinatorial signaling from fibronectin/FGF2 and WNT5a is summarized in the Table 4.

TABLE 4

Composition to create WNT signaling microenvironment surface

| Molecule | SEQUENCE | 2D substrate | 3D substrate (WebTrix™) |
|---|---|---|---|
| Fibronectin | PHSRN-RGDSP (SEQ ID NO: 17) | 0.1 mg/mL | 0.05 mg/mL |
| WNT5a | LGTQGRLCNKTSEGMDGCEL (SEQ ID NO: 48) | 0.1 mg/mL | 0.1 mg/mL |
| FGF2 | WYVALKRTGQKLG (SEQ ID NO: 71) | 0.1 mg/mL | 0.1 mg/mL |
| WNT5a/FGF | LGTQGRLCNKTSEGMDGCEL (SEQ ID NO: 48) - WYVALKRTGQKLG (SEQ ID NO: 71) | 0.1 mg/mL | 0.1 mg/mL |
| TGFβ | LTGKNFPMFHRN (SEQ ID NO: 45) | 0.1 mg/mL | 0.1 mg/mL |
| LIF | IVPLLLLVLH (SEQ ID NO: 49) | 0.1 mg/mL | 0.1 mg/mL |

TABLE 4-continued

Composition to create WNT signaling microenvironment surface

| Molecule | SEQUENCE | 2D substrate | 3D substrate (WebTrix™) |
|---|---|---|---|
| FGF2/ TGFβ | WYVALKRTGQKLG (SEQ ID NO: 71) - LTGKNFPMFHRN (SEQ ID NO: 45) | 0.1 mg/mL | 0.1 mg/mL |
| TGFβ/WNT5a | LTGKNFPMFHRN (SEQ ID NO: 45) - LGTQGRLCNKTSEGMDGCEL (SEQ ID NO: 48) | 0.1 mg/mL | 0.1 mg/mL |
| FGF2/ TGFβ/WNT5a | WYVALKRTGQKLG (SEQ ID NO: 71) - LTGKNFPMFHRN (SEQ ID NO: 45) - LGTQGRLCNKTSEGMDGCEL (SEQ ID NO: 48) | 0.1 mg/mL | 0.1 mg/mL |

Using the composition listed above, 18 different microenvironment surfaces were prepared using EDC/S—NHS as a crosslinking agent as set forth in EXAMPLE 4.

Additionally, to investigate the effect of composition ratio of PHSRN-RGDSP (SEQ ID NO:17)/Wnt or LIF peptide in order to activate integrin/frizzled receptor signaling and integrin/LIF receptor signaling on the self-renewal of human induced pluripotent stem cells, a series of WebTrix™ with four different composition ratios (100/0, 80/20, 50/50, 20/80) were prepared.

Human induced pluripotent stem cells were maintained in serum replacement medium before seeding on to the 18 different microenvironment surfaces. Instead of E6 supplemented growth factor or E8 medium, mTesR (Stem Cell Technologies, Inc.) was used and changed daily. After four days, cells were washed and stained with AP according to the procedure in EXAMPLE 5.

FIG. 8 represented the colony of stem cells cultured on individual microenvironment surface. As shown in FIG. 8A, the shape and size of colony cultured on WebTrix™ was comparable with that of colony cultured on Matrigel™ indicating the cells were self-renewing in undifferentiated state while the shape and size of colony cultured on 2D surface apparently less comparable than that of colony cultured on Matrigel™, it seemed a few cells were partially differentiated if WNT-derived peptide motif was absent.

Figure 8A:
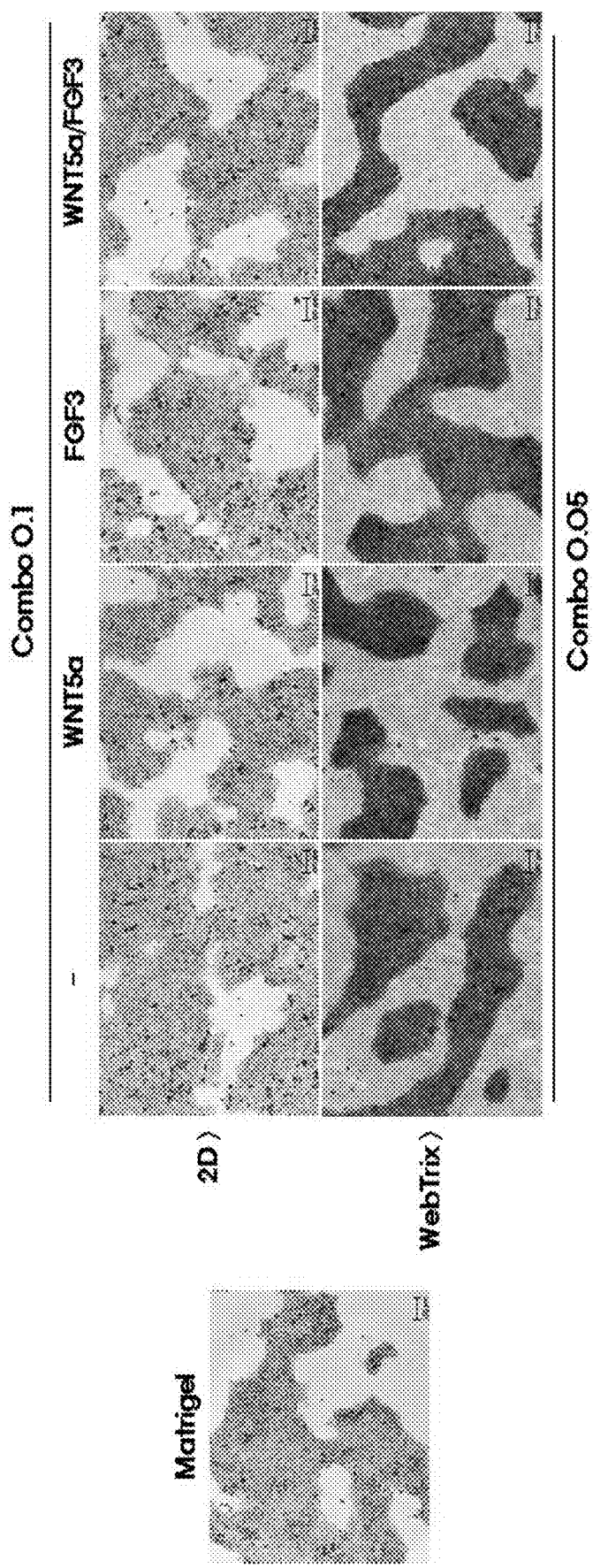
FIGS. 8A-8F represent the colony of stem cells cultured on various biochemical and physical microenvironment signaling surfaces.
Figure 8B:
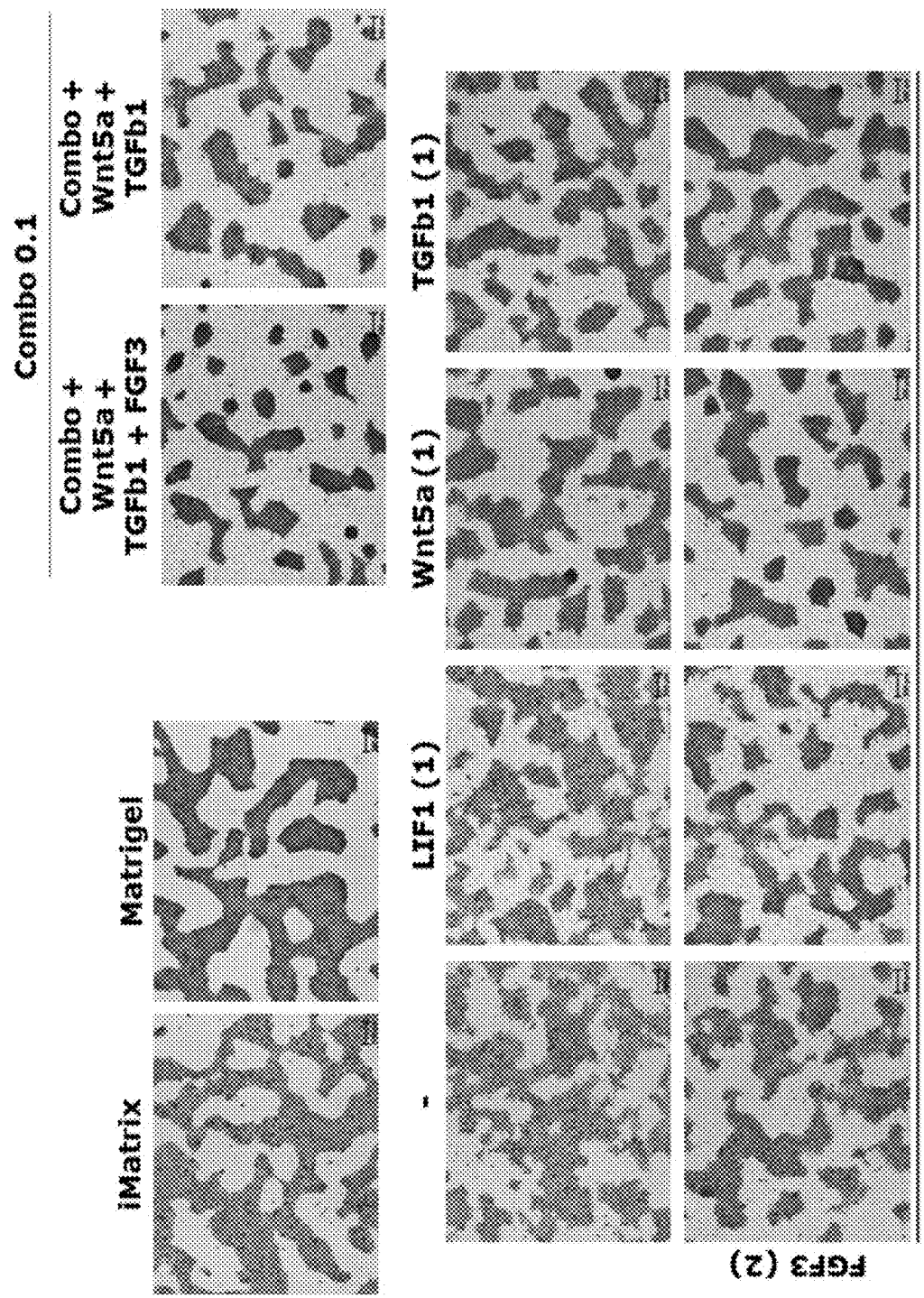
Figure 8C:
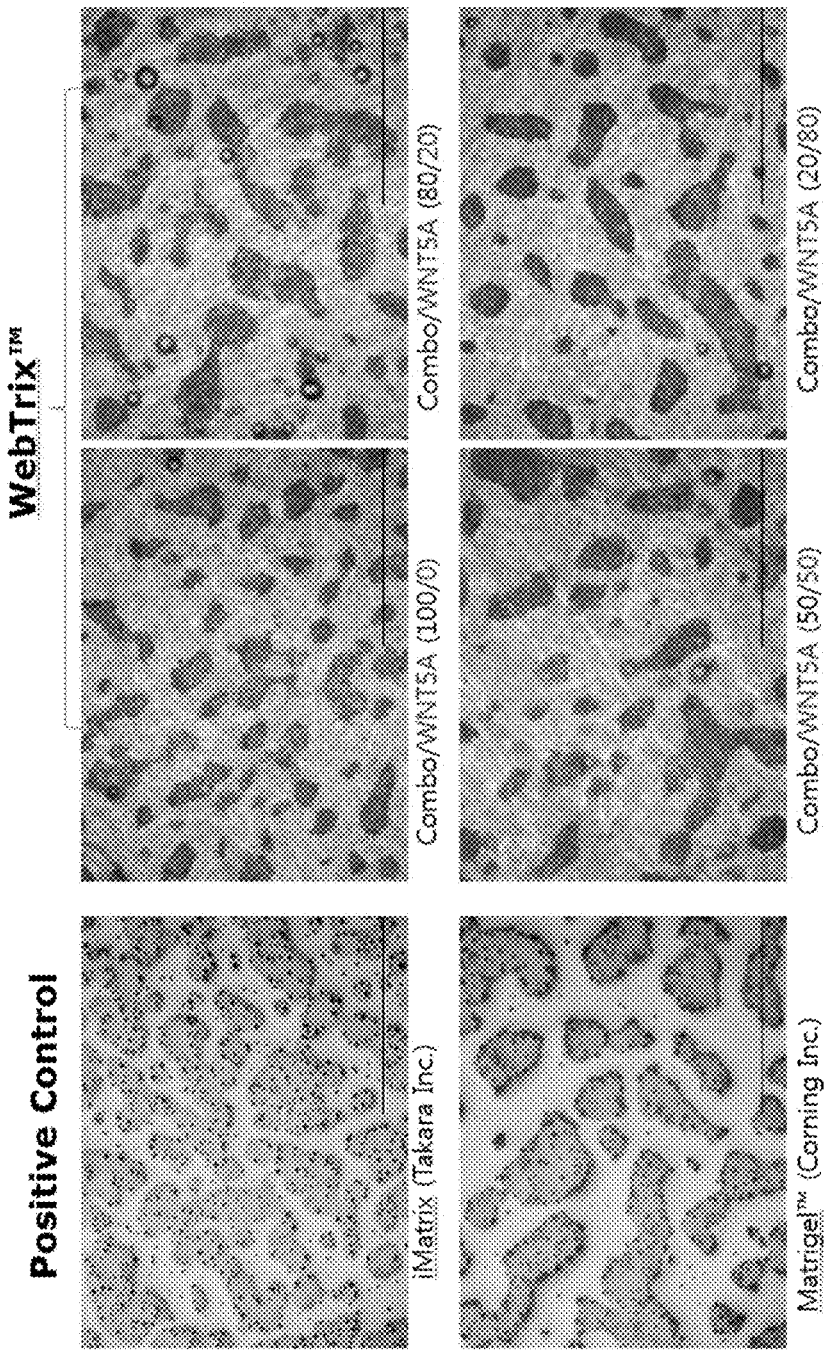
Figure 8D:
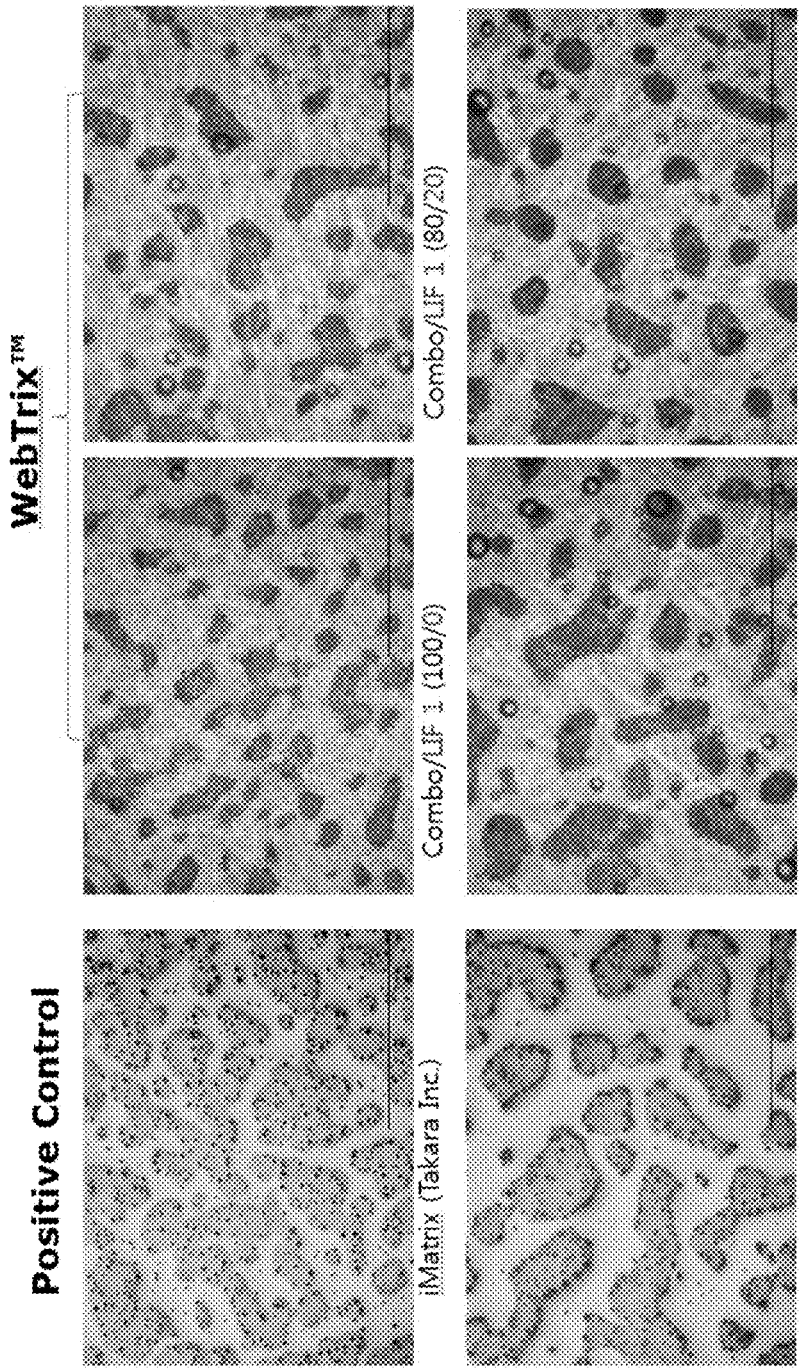

FIGS. 8C and 8D showed the effect of combinatorial signaling of integrin α5β1—frizzled receptor and integrin α5β1—receptor, respectively, on the self-renewal of stem cells. In comparison with the effect of combinatorial signaling of integrin α5β1—growth factor receptor (FGF or TGFβ), both integrin α5β1—frizzled receptor and integrin α5β1—LIF receptor signaling provided more favorable microenvironment for the stem cells self-renewal. Particularly, WebTrix™ with integrin α5β1—frizzled receptor signaling showed better efficacy for stem cells self-renewal and stemness maintenance than Matrigel™.

For the analysis of stemness markers OCT4 and Sox2 expressed when cultured on different microenvironment surface, cells were fixed using 4% paraformaldehyde (Sigma-Aldrich) in 0.5% TRITON® X-100 solution for 30 minutes, accompanied by three times PBS washing, and 10% normal goat serum (Sigma-Aldrich) was added. The monoclonal antibodies against Oct4 (Santa Cruz Biotechnology) diluted at a concentration of 1:1,000 and Sox2 (Santa Cruz Biotechnology) diluted at a concentration of 1:1,000 was added to the above solution. The antibody was reacted for 24 hours at 4° C. and washed with PBS three times with 0.5% TRITON® X-100 added PBS. As the secondary antibody, goat anti-mouse ALEXA FLUOR® 546 (Invitrogen) was diluted with 0.5% TRITON® X-100 added PBS diluted at a concentration of 1:1,000, and reacted for 1.5 hours. Thereafter, the cells were reacted with 10 µg/mL of TO-PRO3 (Invitrogen) for the cell nucleus staining, and observed with fluorescent scanning microscopy (Zeiss).

Figure 8E:
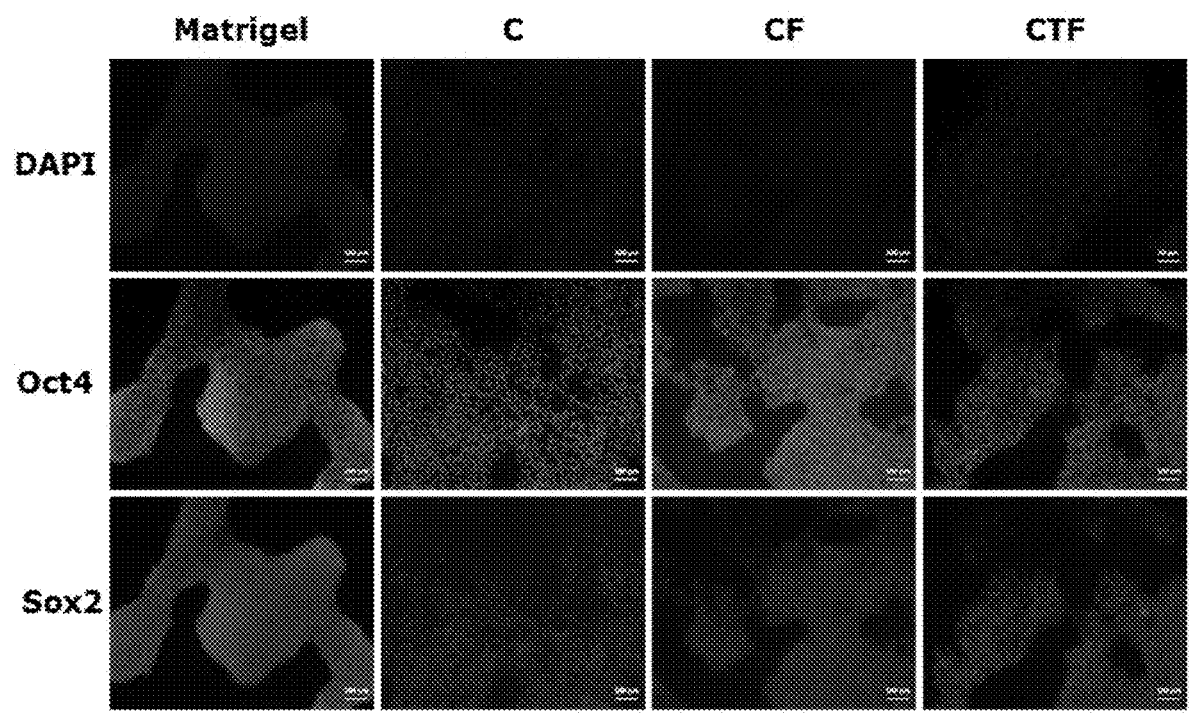
Figure 8F:
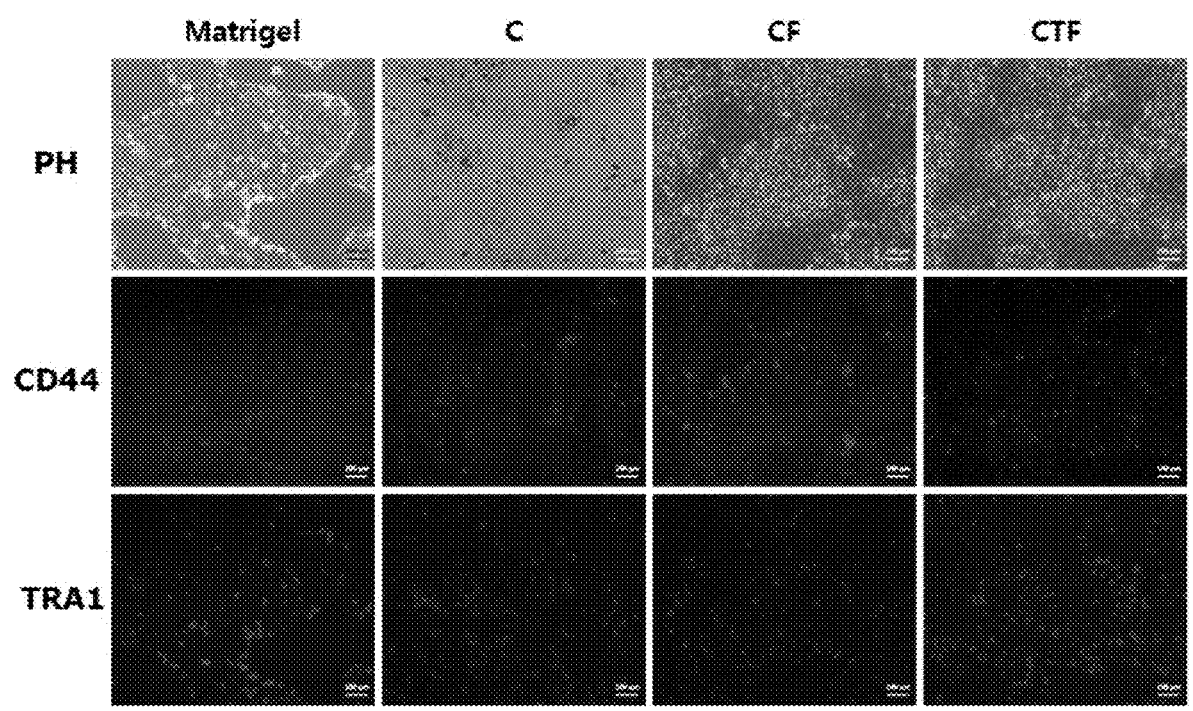

FIG. 8E represented the expression of Oct4 and Sox2, core stemness markers of stemness. As predicted based on the colony size and shape, WebTrix™ with integrin α5β1—TGFβ receptor—FGF receptor signaling provided the most favorable microenvironment for stem cells self-renewal as the expression level of core stemness markers were comparable with Matrigel™.

During the culture period, some of the wells were trypsinized and the cell number was determined on the daily basis using a hemocytometer. The average number for each single day was calculated and the values were used to plot a growth curve for each stem cell.

Figure 9:
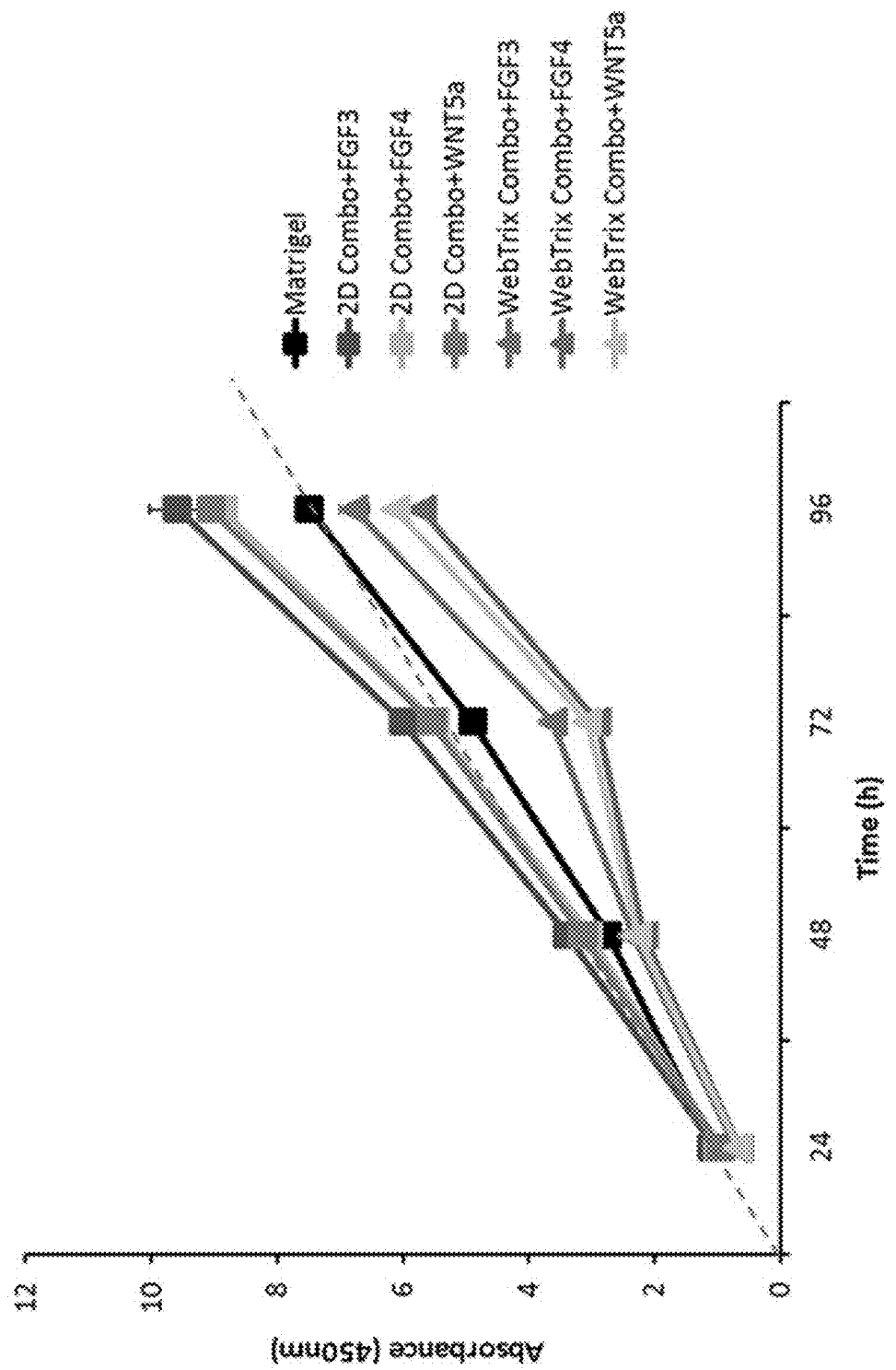
FIG. 9 represents the growth curve of stem cells cultured on different microenvironment surface.

FIG. 9 represented the growth curve of stem cells cultured on different microenvironment surface. As seen from FIG. 9, the growth curve plotted for individual microenvironment surface indicated that the stem cells on the 2D microenvironment surface inducing integrin α5β1—FGF receptor signaling grows faster than those on Matrigel™, but cells on 3D microenvironment surface inducing the same integrin α5β1—FGF receptor signaling grows relatively slow. The presence of WNT signaling may play a role in the stemness maintenance rather than proliferation in consistence with the colony shape and size observed in FIGS. 8C and 8D.

Example 8

Cell Migration Assay

In wound healing or tissue regeneration, cells movement is essential process as a tightly or loosely associated cohesive group, and integrin-based adhesion has served as a model for studying the central role of adhesion in cell migration. Cell migration requires the dynamic interaction between a cell and the substratum on which it is attached and over which it migrates. Optimum cell speed occurs at intermediate levels of expression of α5β1 or α2β1 integrins or intermediate concentrations of ligand, including fibronectin or collagen. In general, in most cell types, there is an intermediate cell-substratum adhesiveness that supports maximum migration.

Generally, integrin α2β1, α3β1 and α5β1 are the key adhesion receptors to regulate cell migration, and α2β1 integrin functions as the major receptor for collagen type I on a large number of different cell types including keratinocytes and fibroblasts.

Figure 11A:
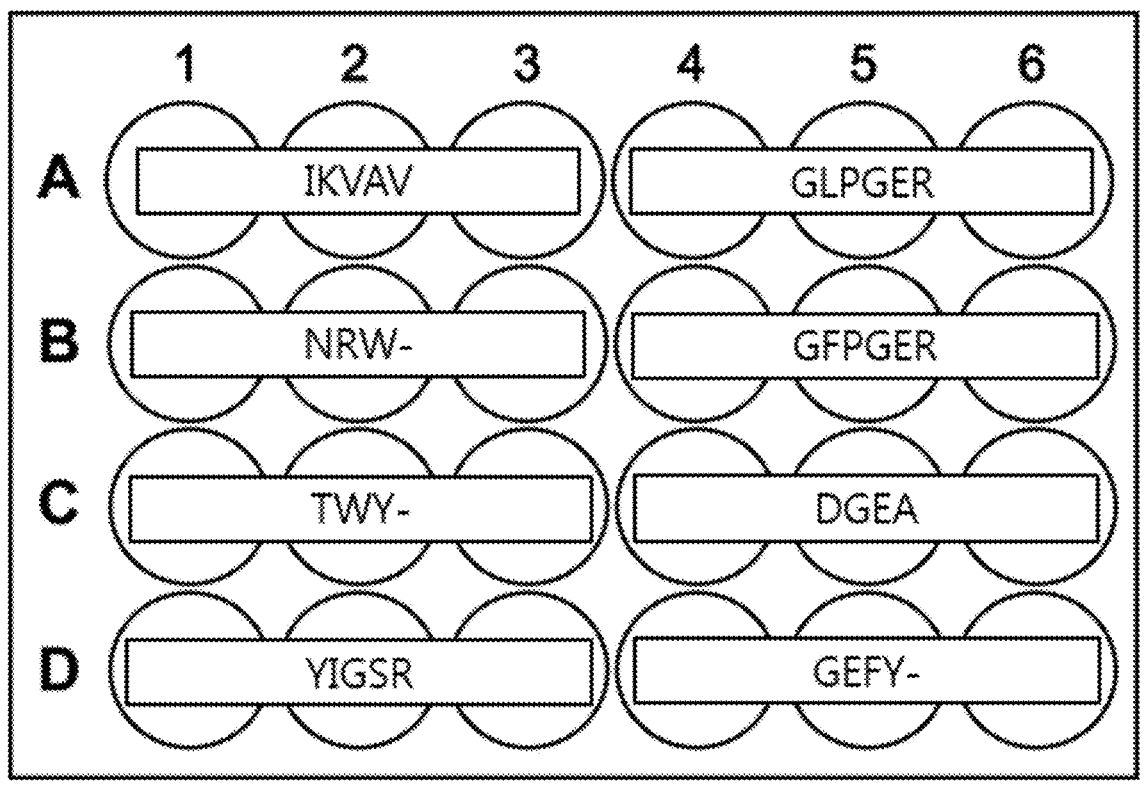
FIG. 11A represents the layout for this cell adhesion and migration assay.
Figure 11B:
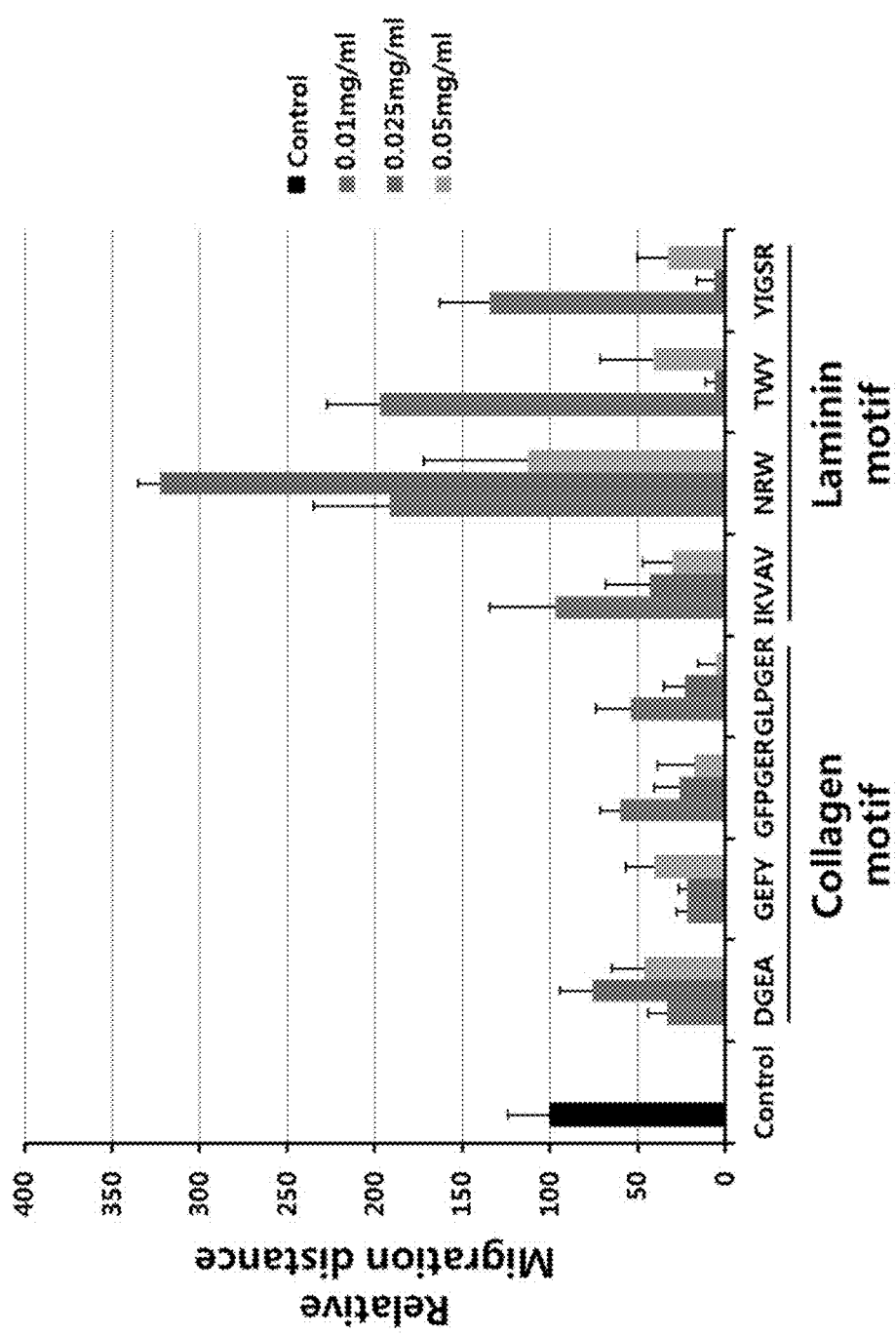
FIG. 11B represents the measurement of migration distance on individual peptide motif coated surface. Specifically, cells A1-A3 are SEQ ID NO:74; cells B1-B3 are SEQ ID NO:75; cells C1-C3 are SEQ ID NO:76; cells D1-D3 are SEQ ID NO:77; cells A4-A6 are SEQ ID NO:78; cells B4-B6 are SEQ ID NO:79; cells C4-C6 are SEQ ID NO:80; and cells D4-D6 are SEQ ID NO:81.

To identify optimal integrin binding peptide motif, a screening for keratinocyte adhesion and migration was performed. Briefly, eight different integrin α2β1 and α3β1 at a concentration of 0.01 mg/mL were coated on a 24-well plate. FIG. 11A represented the layout for this cell adhesion and migration assay, and FIG. 11B represented the measurement of migration distance on individual peptide motif coated surface. As seen in FIG. 11B, laminin-derived α3β1 binding motifs generally promoted the keratinocyte migration. Particularly, NRWHSIYITRFG (SEQ ID NO:34) motif enabled cells to move very fast. As pointed out above, tissue regeneration requires optimal cell speed, and thus combination of collagen-derived peptide motif and laminin-derived peptide motif may provide optimal microenvironment for wound healing at optimal composition ratio.

Example 9

Effect of Particle Size on Stem Cell Culture

Surface topographical cue, one of important physical cues to determine the cell fate, has been considered being a key feature to regulate cell behaviors. In fact, stem cells can interact with underlying material through nanosized integrin receptors. Therefore, the manipulation of topographical cues at a nanoscale level may be employed to regulate the cell fate.

Different particle size embedded in nanofiber sheet, prepared according to the procedure as set forth in EXAMPLE 3, was used to investigate the effect of nanoscale (500 nm) and microscale (500 μm) particle size on human induced pluripotent stem cell behaviors.

Human-induced pluripotent stem cells were maintained in serum replacement media conditions before switching from the serum-free media to the microenvironment surface. The cell clusters were seeded on the microenvironment surface in mTeSR™ (Stem Cell Technologies). Medium was changed daily. After four days, cells were washed and fixed for AP staining according to the procedure as set forth in EXAMPLE 5.

Figure 10A:
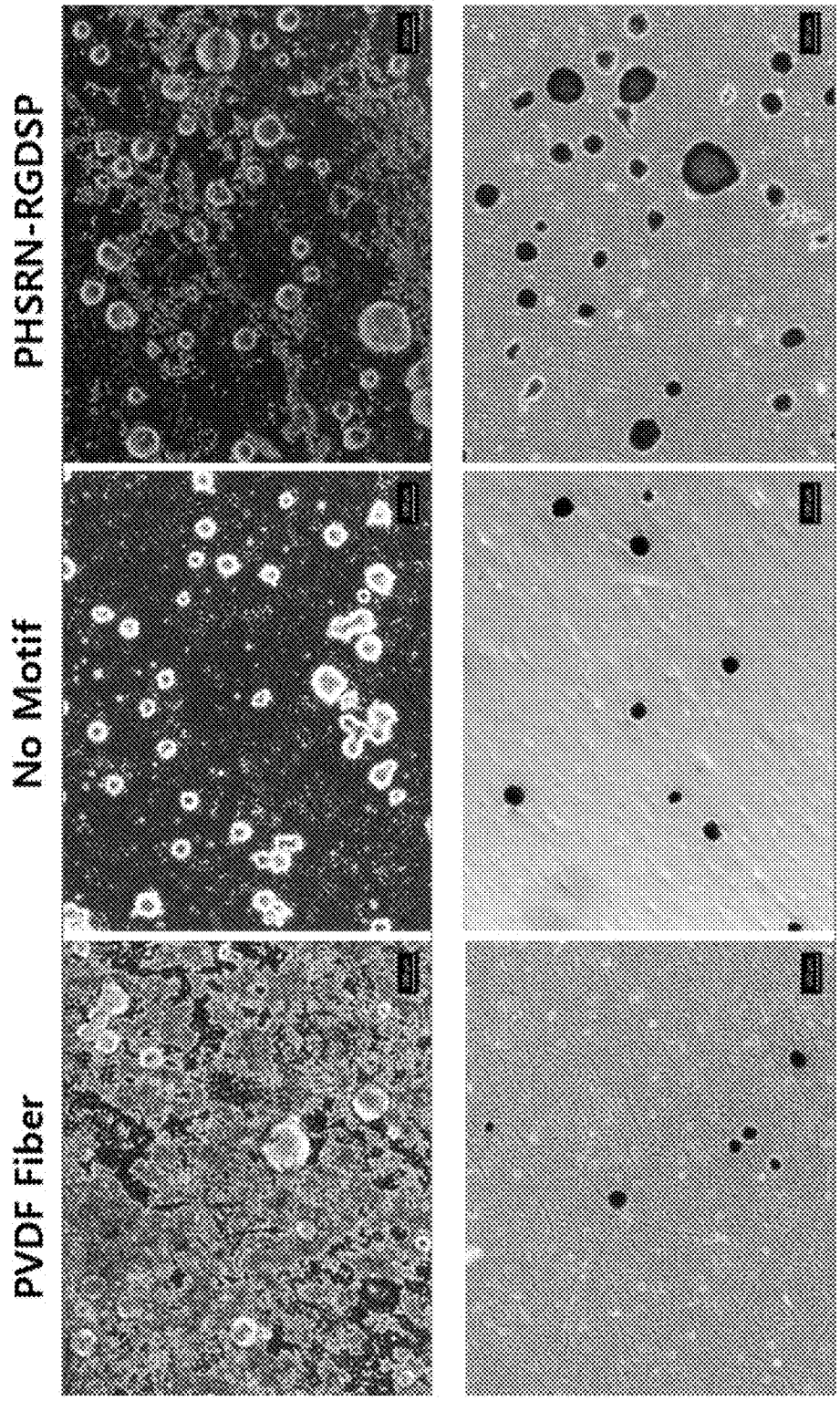
FIGS. 10A and 10B represent the effect of particle size on the stemness and proliferation of human induced pluripotent stem cells in comparison with nanofiber only, and nanofiber containing integrin α5β1 binding motif (PHSRN-RGDSP (SEQ ID NO:17)). Both FIGS. 10A and 10B contain SEQ ID NO:17.
Figure 10B:
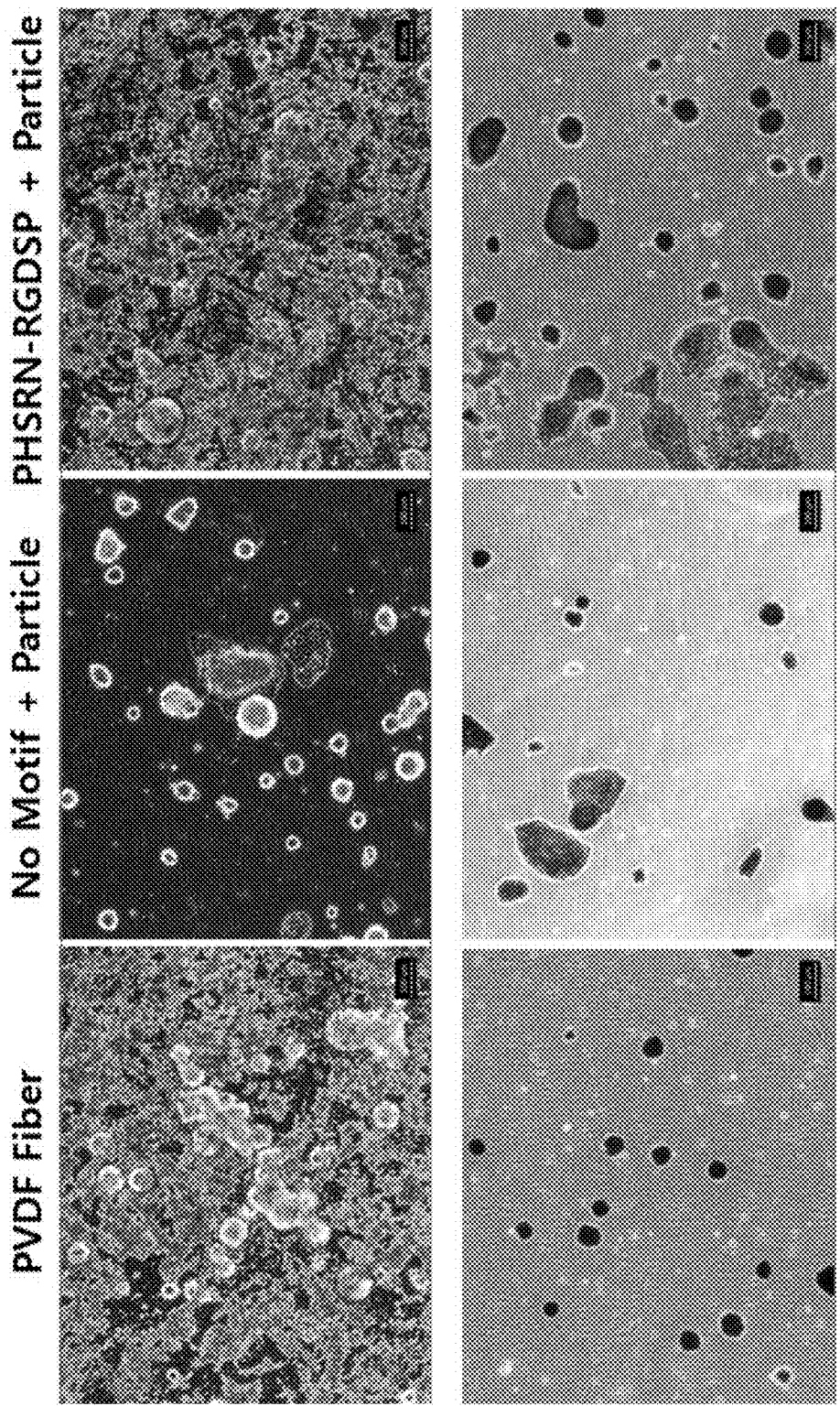

The results are shown in FIG. 10. The effect of nanoparticle size of 500 nm and 500 μm on stemness maintenance and growth was presented in FIGS. 10A and 10B, respectively. The size of colony cultured on microscale particle presenting surface was bigger than that of colony cultured on nanoscale particle size surface as seen in FIG. 10. However, compared to the size of colony cultured on the same nanofiber sheet (0.1 mg/ml) without particles as seen in FIG. 6 where colony-of-partially-differentiated stem cells observed on the surface prepared from the concentration lower than 0.1 mg/ml, it is clear that the presence of particle size supports the stemness maintenance.

Example 10

Antimicrobial Microenvironment

A series of antimicrobial nanofiber sheet with varying surface density of antimicrobial peptide motif, KLWKKWAKKWLKLWKA (SEQ ID NO:59) was prepared according to EXAMPLE 1. To control the surface density of antimicrobial peptide motif, A gram negative bacterium (*E. coli*) and a gram-positive bacterium *Staphylococcus aureus* (SA) were used to evaluate the antimicrobial activity of the nanofiber sheet. The antimicrobial activity of the nanosheet was determined by JIS Z 2801:2000, described by Haldar et al., *Nature Protocols* 2007, 2(19):2412.

Figure 12A:
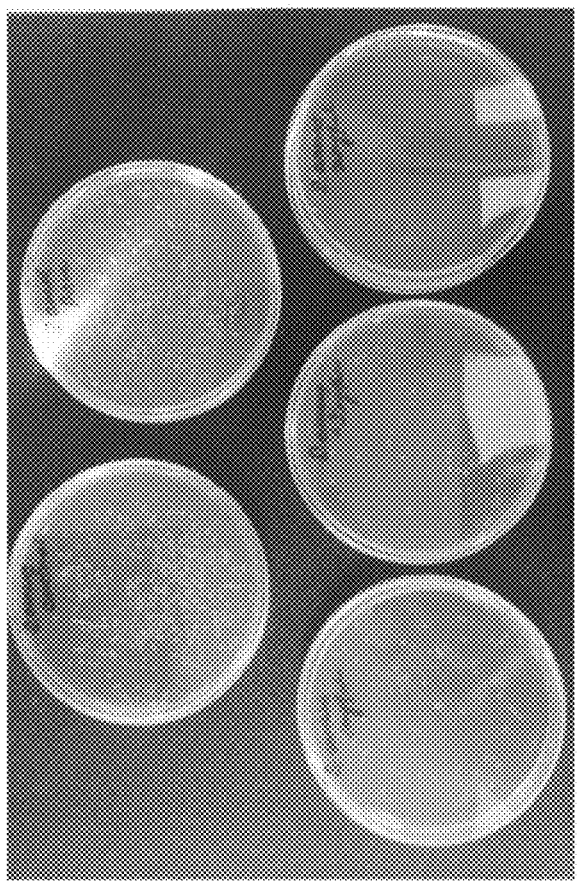
FIG. 12A shows the antimicrobial nanofiber surface effectively inhibited the growth of bacteria.

After the nanofiber sheet is inoculated by two bacteria (*E. coli* and SA), the colony-forming unit (CFU) of both bacteria was counted. As seen in FIG. 12A, both nanofiber sheet of bare PVDF and no antimicrobial peptide presenting PVDF nanofiber sheet did not inhibit the growth of bacteria, but antimicrobial peptide presenting nanofiber sheet showed effectively inhibited the growth of bacteria.

Figure 12A:
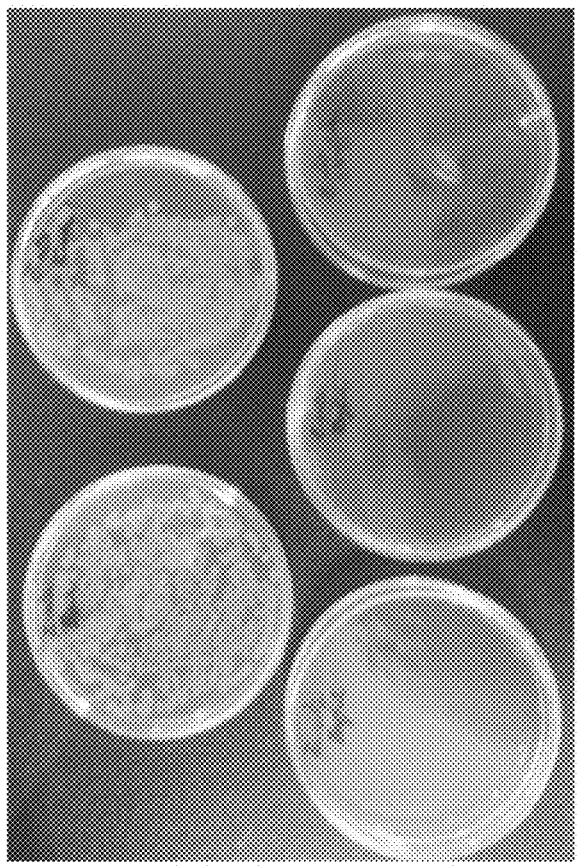
Figure 12B:
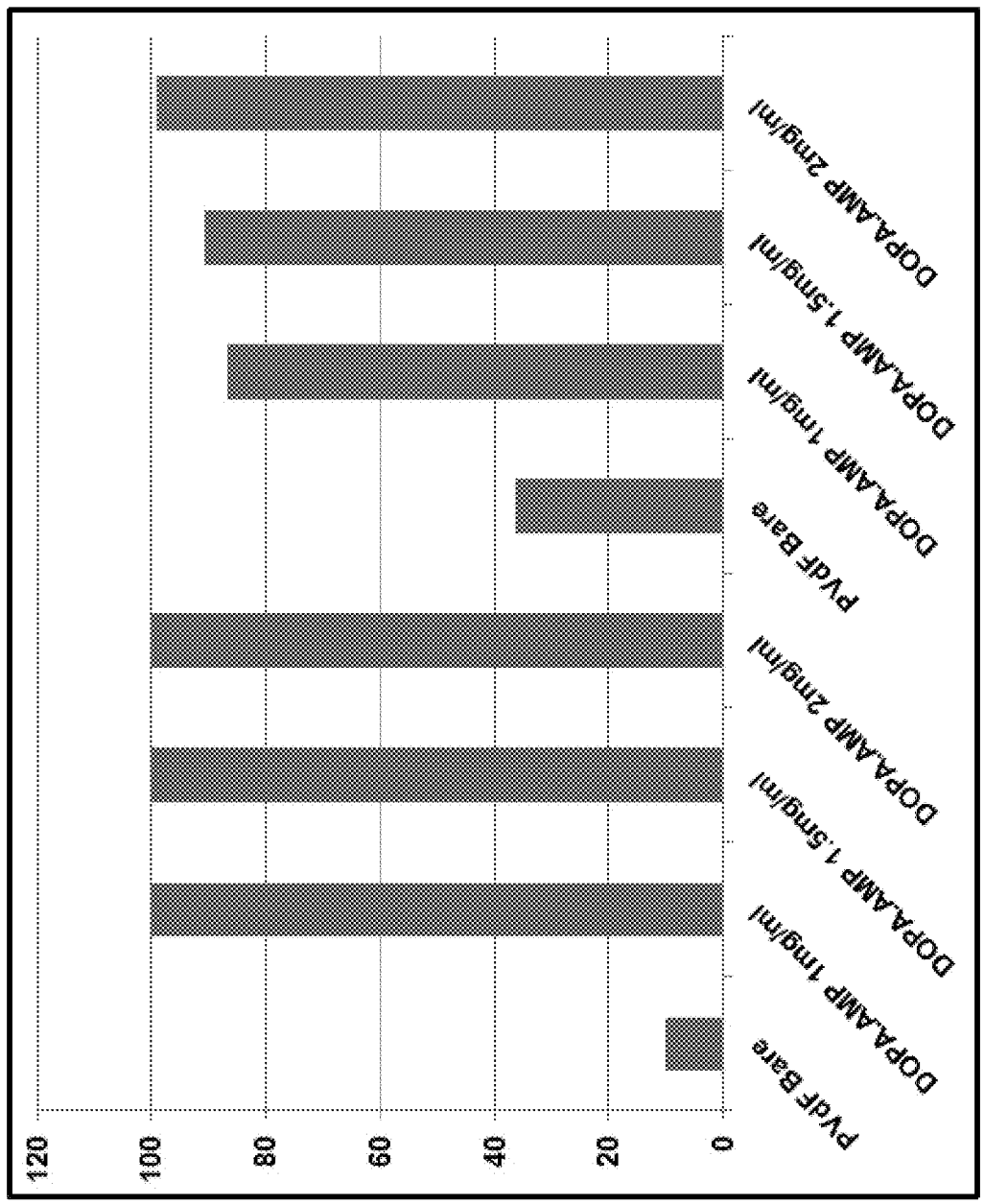
FIG. 12B represents that the efficacy of antimicrobial peptide presenting nanofiber sheet, indicating the antimicrobial nanofiber surface may be used for cell culture system without the use of antibiotics.

FIG. 12B shows that the efficacy of antimicrobial peptide presenting nanofiber sheet. As seen in FIG. 12, the antimicrobial activity of nanofiber sheet showed concentration dependent for SA, but effectively kill *E. coli* even at low concentration (1 mg/mL).

What is claimed is:

1. A microenvironment for culturing cells, wherein the microenvironment comprises: an adhesion receptor binding motif and a co-receptor binding motif, wherein the adhesion receptor binding motif and the co-receptor binding motif regulate cellular behavior of cells cultured on the microenvironment via combinatorial signaling generating from crosstalk between an adhesion receptor and a co-receptor so as to enhance self-renewal and/or proliferation of cells cultured on the microenvironment, wherein the adhesion receptor binding motif comprises SEQ ID NO: 17, and wherein the co-receptor binding motif is selected from the group consisting of SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 47, SEQ ID NO: 48, SEQ ID NO: 49, and SEQ ID NO: 50.

* * * * *

SEQUENCE LISTING

```
<160> NUMBER OF SEQ ID NOS: 81

<210> SEQ ID NO 1
<211> LENGTH: 10
<212> TYPE: PRT
<213> ORGANISM: Artificial Sequence
<220> FEATURE:
<223> OTHER INFORMATION: model peptide of the tandem repeat decapeptide
      derived from foot protein 1 (FP-1, Mytilus edulis)

<400> SEQUENCE: 1

Ala Lys Pro Ser Tyr Pro Pro Thr Tyr Lys
1               5                   10

<210> SEQ ID NO 2
<211> LENGTH: 20
<212> TYPE: PRT
<213> ORGANISM: Artificial Sequence
<220> FEATURE:
<223> OTHER INFORMATION: 2 times repeated sequence derived from foot
      protein 1 (FP-1, Mytilus edulis)

<400> SEQUENCE: 2

Ala Lys Pro Ser Tyr Pro Pro Thr Tyr Lys Ala Lys Pro Ser Tyr Pro
1               5                   10                  15
```

Pro Thr Tyr Lys
          20

<210> SEQ ID NO 3
<211> LENGTH: 60
<212> TYPE: PRT
<213> ORGANISM: Artificial Sequence
<220> FEATURE:
<223> OTHER INFORMATION: 6 times repeated sequence derived from foot
      protein 1 (FP-1, Mytilus edulis)

<400> SEQUENCE: 3

Ala Lys Pro Ser Tyr Pro Pro Thr Tyr Lys Ala Lys Pro Ser Tyr Pro
1               5                   10                  15

Pro Thr Tyr Lys Ala Lys Pro Ser Tyr Pro Pro Thr Tyr Lys Ala Lys
            20                  25                  30

Pro Ser Tyr Pro Pro Thr Tyr Lys Ala Lys Pro Ser Tyr Pro Pro Thr
        35                  40                  45

Tyr Lys Ala Lys Pro Ser Tyr Pro Pro Thr Tyr Lys
    50                  55                  60

<210> SEQ ID NO 4
<211> LENGTH: 39
<212> TYPE: PRT
<213> ORGANISM: Artificial Sequence
<220> FEATURE:
<223> OTHER INFORMATION: partial sequence of foot protein type 2 (FP-2,
      Mytilus californianus)

<400> SEQUENCE: 4

Glu Val His Ala Cys Lys Pro Asn Pro Cys Lys Asn Asn Gly Arg Cys
1               5                   10                  15

Tyr Pro Asp Gly Lys Thr Gly Tyr Lys Cys Lys Cys Val Gly Gly Tyr
            20                  25                  30

Ser Gly Pro Thr Cys Ala Cys
        35

<210> SEQ ID NO 5
<211> LENGTH: 52
<212> TYPE: PRT
<213> ORGANISM: Artificial Sequence
<220> FEATURE:
<223> OTHER INFORMATION: Foot protein type 3 (FP-3, Mytilus edulis)

<400> SEQUENCE: 5

Ala Asp Tyr Tyr Gly Pro Lys Tyr Gly Pro Pro Arg Arg Tyr Gly Gly
1               5                   10                  15

Gly Asn Tyr Asn Arg Tyr Gly Gly Ser Arg Arg Tyr Gly Gly Tyr Lys
            20                  25                  30

Gly Trp Asn Asn Gly Trp Lys Arg Gly Arg Trp Gly Arg Lys Tyr Tyr
        35                  40                  45

Glu Phe Glu Phe
    50

<210> SEQ ID NO 6
<211> LENGTH: 46
<212> TYPE: PRT
<213> ORGANISM: Artificial Sequence
<220> FEATURE:
<223> OTHER INFORMATION: Foot protein type 3 (FP-3, Mytilus
      galloprovincialis : mgfp-3A)

<400> SEQUENCE: 6

```
Ala Asp Tyr Tyr Gly Pro Lys Tyr Gly Pro Pro Arg Arg Tyr Gly Gly
1               5                   10                  15

Gly Asn Tyr Asn Arg Tyr Gly Arg Arg Tyr Gly Gly Tyr Lys Gly Trp
                20                  25                  30

Asn Asn Gly Trp Lys Arg Gly Arg Trp Gly Arg Lys Tyr Tyr
            35                  40                  45
```

<210> SEQ ID NO 7
<211> LENGTH: 60
<212> TYPE: PRT
<213> ORGANISM: Artificial Sequence
<220> FEATURE:
<223> OTHER INFORMATION: partial sequence from foot protein type 4
      (Mytilus californianus)

<400> SEQUENCE: 7

```
Gly His Val His Arg His Arg Val Leu His Lys His Val His Asn His
1               5                   10                  15

Arg Val Leu His Lys His Leu His Lys His Gln Val Leu His Gly His
                20                  25                  30

Val His Arg His Gln Val Leu His Lys His Val His Asn His Arg Val
            35                  40                  45

Leu His Lys His Leu His Lys His Gln Val Leu His
        50                  55                  60
```

<210> SEQ ID NO 8
<211> LENGTH: 75
<212> TYPE: PRT
<213> ORGANISM: Artificial Sequence
<220> FEATURE:
<223> OTHER INFORMATION: Foot protein type5 (FP-5, Mytilus edulis)

<400> SEQUENCE: 8

```
Ser Ser Glu Glu Tyr Lys Gly Gly Tyr Tyr Pro Gly Asn Ala Tyr His
1               5                   10                  15

Tyr His Ser Gly Gly Ser Tyr His Gly Ser Gly Tyr His Gly Gly Tyr
                20                  25                  30

Lys Gly Lys Tyr Tyr Gly Lys Ala Lys Lys Tyr Tyr Tyr Lys Tyr Lys
            35                  40                  45

Asn Ser Gly Lys Tyr Lys Tyr Leu Lys Lys Ala Arg Lys Tyr His Arg
        50                  55                  60

Lys Gly Tyr Lys Lys Tyr Tyr Gly Gly Ser Ser
65                  70                  75
```

<210> SEQ ID NO 9
<211> LENGTH: 76
<212> TYPE: PRT
<213> ORGANISM: Artificial Sequence
<220> FEATURE:
<223> OTHER INFORMATION: Foot protein 5 (FP-5, Mytilus edulis)

<400> SEQUENCE: 9

```
Ser Ser Glu Glu Tyr Lys Gly Gly Tyr Tyr Pro Gly Asn Thr Tyr His
1               5                   10                  15

Tyr His Ser Gly Gly Ser Tyr His Gly Ser Gly Tyr His Gly Gly Tyr
                20                  25                  30

Lys Gly Lys Tyr Tyr Gly Lys Ala Lys Lys Tyr Tyr Tyr Lys Tyr Lys
            35                  40                  45

Asn Ser Gly Lys Tyr Lys Tyr Leu Lys Lys Ala Arg Lys Tyr His Arg
        50                  55                  60
```

```
Lys Gly Tyr Lys Lys Tyr Tyr Gly Gly Gly Ser Ser
 65                  70                  75
```

<210> SEQ ID NO 10
<211> LENGTH: 71
<212> TYPE: PRT
<213> ORGANISM: Artificial Sequence
<220> FEATURE:
<223> OTHER INFORMATION: Foot protein 5 (FP-5, Mytilus coruscus)

<400> SEQUENCE: 10

```
Tyr Asp Asp Tyr Ser Asp Gly Tyr Tyr Pro Gly Ser Ala Tyr Asn Tyr
 1               5                  10                  15

Pro Ser Gly Ser His Trp His Gly His Gly Tyr Lys Gly Lys Tyr Tyr
             20                  25                  30

Gly Lys Gly Lys Lys Tyr Tyr Lys Phe Lys Arg Thr Gly Lys Tyr
             35                  40                  45

Lys Tyr Leu Lys Lys Ala Arg Lys Tyr His Arg Lys Gly Tyr Lys Lys
         50                  55                  60

His Tyr Gly Gly Ser Ser Ser
 65                  70
```

<210> SEQ ID NO 11
<211> LENGTH: 76
<212> TYPE: PRT
<213> ORGANISM: Artificial Sequence
<220> FEATURE:
<223> OTHER INFORMATION: mussel adhesive protein foot protein type5 from
      (Mytilus galloprovincialis)

<400> SEQUENCE: 11

```
Ser Ser Glu Glu Tyr Lys Gly Gly Tyr Tyr Pro Gly Asn Thr Tyr His
 1               5                  10                  15

Tyr His Ser Gly Gly Ser Tyr His Gly Ser Gly Tyr His Gly Tyr
             20                  25                  30

Lys Gly Lys Tyr Tyr Gly Lys Ala Lys Lys Tyr Tyr Lys Tyr Lys
             35                  40                  45

Asn Ser Gly Lys Tyr Lys Tyr Leu Lys Lys Ala Arg Lys Tyr His Arg
         50                  55                  60

Lys Gly Tyr Lys Lys Tyr Tyr Gly Gly Gly Ser Ser
 65                  70                  75
```

<210> SEQ ID NO 12
<211> LENGTH: 99
<212> TYPE: PRT
<213> ORGANISM: Artificial Sequence
<220> FEATURE:
<223> OTHER INFORMATION: mussel adhesive protein foot protein type 6

<400> SEQUENCE: 12

```
Gly Gly Gly Asn Tyr Arg Gly Tyr Cys Ser Asn Lys Gly Cys Arg Ser
 1               5                  10                  15

Gly Tyr Ile Phe Tyr Asp Asn Arg Gly Phe Cys Lys Tyr Gly Ser Ser
             20                  25                  30

Ser Tyr Lys Tyr Asp Cys Gly Asn Tyr Ala Gly Cys Cys Leu Pro Arg
             35                  40                  45

Asn Pro Tyr Gly Arg Val Lys Tyr Tyr Cys Thr Lys Lys Tyr Ser Cys
         50                  55                  60

Pro Asp Asp Phe Tyr Tyr Tyr Asn Asn Lys Gly Tyr Tyr Tyr Tyr Asn
 65                  70                  75                  80
```

```
Asp Lys Asp Tyr Phe Asn Cys Gly Ser Tyr Asn Gly Cys Cys Leu Arg
                85                  90                  95

Ser Gly Tyr

<210> SEQ ID NO 13
<211> LENGTH: 194
<212> TYPE: PRT
<213> ORGANISM: Artificial Sequence
<220> FEATURE:
<223> OTHER INFORMATION: hybrid mussel adhesive protein (FP-151, MEFP-5
      based: Kollodis)

<400> SEQUENCE: 13

Ala Lys Pro Ser Tyr Pro Pro Thr Tyr Lys Ala Lys Pro Ser Tyr Pro
1               5                   10                  15

Pro Thr Tyr Lys Ala Lys Pro Ser Tyr Pro Pro Thr Tyr Lys Ala Lys
            20                  25                  30

Pro Ser Tyr Pro Pro Thr Tyr Lys Ala Lys Pro Ser Tyr Pro Pro Thr
        35                  40                  45

Tyr Lys Ala Lys Pro Ser Tyr Pro Pro Thr Tyr Lys Ser Ser Glu Glu
    50                  55                  60

Tyr Lys Gly Gly Tyr Tyr Pro Gly Asn Ala Tyr His Tyr His Ser Gly
65                  70                  75                  80

Gly Ser Tyr His Gly Ser Gly Tyr His Gly Gly Tyr Lys Gly Lys Tyr
                85                  90                  95

Tyr Gly Lys Ala Lys Lys Tyr Tyr Tyr Lys Tyr Lys Asn Ser Gly Lys
            100                 105                 110

Tyr Lys Tyr Leu Lys Lys Ala Arg Lys Tyr His Arg Lys Gly Tyr Lys
        115                 120                 125

Tyr Tyr Gly Gly Ser Ser Ala Lys Pro Ser Tyr Pro Pro Thr Tyr Lys
    130                 135                 140

Ala Lys Pro Ser Tyr Pro Pro Thr Tyr Lys Ala Lys Pro Ser Tyr Pro
145                 150                 155                 160

Pro Thr Tyr Lys Ala Lys Pro Ser Tyr Pro Pro Thr Tyr Lys Ala Lys
                165                 170                 175

Pro Ser Tyr Pro Pro Thr Tyr Lys Ala Lys Pro Ser Tyr Pro Pro Thr
            180                 185                 190

Tyr Lys

<210> SEQ ID NO 14
<211> LENGTH: 196
<212> TYPE: PRT
<213> ORGANISM: Artificial Sequence
<220> FEATURE:
<223> OTHER INFORMATION: hybrid mussel adhesive protein (FP-151, MGFP-5
      based)

<400> SEQUENCE: 14

Ala Lys Pro Ser Tyr Pro Pro Thr Tyr Lys Ala Lys Pro Ser Tyr Pro
1               5                   10                  15

Pro Thr Tyr Lys Ala Lys Pro Ser Tyr Pro Pro Thr Tyr Lys Ala Lys
            20                  25                  30

Pro Ser Tyr Pro Pro Thr Tyr Lys Ala Lys Pro Ser Tyr Pro Pro Thr
        35                  40                  45

Tyr Lys Ala Lys Pro Ser Tyr Pro Pro Thr Tyr Lys Ser Ser Glu Glu
    50                  55                  60

Tyr Lys Gly Gly Tyr Tyr Pro Gly Asn Thr Tyr His Tyr His Ser Gly
```

```
                65                  70                  75                  80
Gly Ser Tyr His Gly Ser Gly Tyr His Gly Gly Tyr Lys Gly Lys Tyr
                    85                  90                  95
Tyr Gly Lys Ala Lys Lys Tyr Tyr Lys Tyr Lys Asn Ser Gly Lys
                100                 105                 110
Tyr Lys Tyr Leu Lys Lys Ala Arg Lys Tyr His Arg Lys Gly Tyr Lys
                115                 120                 125
Lys Tyr Tyr Gly Gly Ser Ser Ala Lys Pro Ser Tyr Pro Pro Thr
            130                 135                 140
Tyr Lys Ala Lys Pro Ser Tyr Pro Pro Thr Tyr Lys Ala Lys Pro Ser
145                 150                 155                 160
Tyr Pro Pro Thr Tyr Lys Ala Lys Pro Ser Tyr Pro Pro Thr Tyr Lys
                165                 170                 175
Ala Lys Pro Ser Tyr Pro Pro Thr Tyr Lys Ala Lys Pro Ser Tyr Pro
            180                 185                 190
Pro Thr Tyr Lys
        195

<210> SEQ ID NO 15
<211> LENGTH: 3
<212> TYPE: PRT
<213> ORGANISM: Artificial Sequence
<220> FEATURE:
<223> OTHER INFORMATION: Fibronectin-derived peptide (RGD)

<400> SEQUENCE: 15

Arg Gly Asp
1

<210> SEQ ID NO 16
<211> LENGTH: 6
<212> TYPE: PRT
<213> ORGANISM: Artificial Sequence
<220> FEATURE:
<223> OTHER INFORMATION: Fibronectin-derived peptide (GRGDSP)

<400> SEQUENCE: 16

Gly Arg Gly Asp Ser Pro
1               5

<210> SEQ ID NO 17
<211> LENGTH: 10
<212> TYPE: PRT
<213> ORGANISM: Artificial Sequence
<220> FEATURE:
<223> OTHER INFORMATION: Fibronectin-derived peptide (PHSRN-RGDSP)

<400> SEQUENCE: 17

Pro His Ser Arg Asn Arg Gly Asp Ser Pro
1               5                   10

<210> SEQ ID NO 18
<211> LENGTH: 9
<212> TYPE: PRT
<213> ORGANISM: Artificial Sequence
<220> FEATURE:
<223> OTHER INFORMATION: Fibronectin-derived peptide (SPPRRARVT)

<400> SEQUENCE: 18

Ser Pro Pro Arg Arg Ala Arg Val Thr
1               5
```

```
<210> SEQ ID NO 19
<211> LENGTH: 8
<212> TYPE: PRT
<213> ORGANISM: Artificial Sequence
<220> FEATURE:
<223> OTHER INFORMATION: Fibronectin-derived peptide (WQPPRARI)

<400> SEQUENCE: 19

Trp Gln Pro Pro Arg Ala Arg Ile
1               5

<210> SEQ ID NO 20
<211> LENGTH: 15
<212> TYPE: PRT
<213> ORGANISM: Artificial Sequence
<220> FEATURE:
<223> OTHER INFORMATION: Fibronectin-derived peptide (KNNQKSEPLIGRKKT)

<400> SEQUENCE: 20

Lys Asn Asn Gln Lys Ser Glu Pro Leu Ile Gly Arg Lys Lys Thr
1               5                   10                  15

<210> SEQ ID NO 21
<211> LENGTH: 12
<212> TYPE: PRT
<213> ORGANISM: Artificial Sequence
<220> FEATURE:
<223> OTHER INFORMATION: Laminin-derived peptide (RKRLQVQLSIRT)

<400> SEQUENCE: 21

Arg Lys Arg Leu Gln Val Gln Leu Ser Ile Arg Thr
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Laminin-derived peptide (GKNTGDHFVLYM)

<400> SEQUENCE: 22

Gly Lys Asn Thr Gly Asp His Phe Val Leu Tyr Met
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Laminin-derived peptide (VVSLYNFEQTFML)

<400> SEQUENCE: 23

Val Val Ser Leu Tyr Asn Phe Glu Gln Thr Phe Met Leu
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Laminin-derived peptide (RFDQELRLVSYN)

<400> SEQUENCE: 24

Arg Phe Asp Gln Glu Leu Arg Leu Val Ser Tyr Asn
1               5                   10

<210> SEQ ID NO 25
```

-continued

```
<211> LENGTH: 13
<212> TYPE: PRT
<213> ORGANISM: Artificial Sequence
<220> FEATURE:
<223> OTHER INFORMATION: Laminin-derived peptide (RLVSYSGVLFFLK)

<400> SEQUENCE: 25

Arg Leu Val Ser Tyr Ser Gly Val Leu Phe Phe Leu Lys
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Laminin-derived peptide (ASKAIQVFLLGG)

<400> SEQUENCE: 26

Ala Ser Lys Ala Ile Gln Val Phe Leu Leu Gly Gly
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Laminin-derived peptide (VLVRVERATVFS)

<400> SEQUENCE: 27

Val Leu Val Arg Val Glu Arg Ala Thr Val Phe Ser
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Laminin-derived peptide (TVFSVDQDNMLE)

<400> SEQUENCE: 28

Thr Val Phe Ser Val Asp Gln Asp Asn Met Leu Glu
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Laminin-derived peptide (RLRGPQRVFDLH)

<400> SEQUENCE: 29

Arg Leu Arg Gly Pro Gln Arg Val Phe Asp Leu His
1               5                   10

<210> SEQ ID NO 30
<211> LENGTH: 11
<212> TYPE: PRT
<213> ORGANISM: Artificial Sequence
<220> FEATURE:
<223> OTHER INFORMATION: Laminin-derived peptide (FDLHQNMGSVN)

<400> SEQUENCE: 30

Phe Asp Leu His Gln Asn Met Gly Ser Val Asn
1               5                   10

<210> SEQ ID NO 31
<211> LENGTH: 12
```

```
<212> TYPE: PRT
<213> ORGANISM: Artificial Sequence
<220> FEATURE:
<223> OTHER INFORMATION: Laminin-derived peptide (QQNLGSVNVSTG)

<400> SEQUENCE: 31

Gln Gln Asn Leu Gly Ser Val Asn Val Ser Thr Gly
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Laminin-derived (SRATAQKVSRRS)

<400> SEQUENCE: 32

Ser Arg Ala Thr Ala Gln Lys Val Ser Arg Arg Ser
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Laminin-derived peptide (TWYKIAFQRNRK)

<400> SEQUENCE: 33

Thr Trp Tyr Lys Ile Ala Phe Gln Arg Asn Arg Lys
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Laminin-derived peptide (NRWHSIYITRFG)

<400> SEQUENCE: 34

Asn Arg Trp His Ser Ile Tyr Ile Thr Arg Phe Gly
1               5                   10

<210> SEQ ID NO 35
<211> LENGTH: 16
<212> TYPE: PRT
<213> ORGANISM: Artificial Sequence
<220> FEATURE:
<223> OTHER INFORMATION: FGF1-derived (TGQYLAMDTDGLLYGS)

<400> SEQUENCE: 35

Thr Gly Gln Tyr Leu Ala Met Asp Thr Asp Gly Leu Leu Tyr Gly Ser
1               5                   10                  15

<210> SEQ ID NO 36
<211> LENGTH: 14
<212> TYPE: PRT
<213> ORGANISM: Artificial Sequence
<220> FEATURE:
<223> OTHER INFORMATION: FGF1-derived (WFVGLKKNGSCKRG)

<400> SEQUENCE: 36

Trp Phe Val Gly Leu Lys Lys Asn Gly Ser Cys Lys Arg Gly
1               5                   10

<210> SEQ ID NO 37
<211> LENGTH: 16
<212> TYPE: PRT
```

```
<213> ORGANISM: Artificial Sequence
<220> FEATURE:
<223> OTHER INFORMATION: FGF2-derived peptide (ANRYLAMKEDGRLLAS)

<400> SEQUENCE: 37

Ala Asn Arg Tyr Leu Ala Met Lys Glu Asp Gly Arg Leu Leu Ala Ser
1               5                   10                  15

<210> SEQ ID NO 38
<211> LENGTH: 10
<212> TYPE: PRT
<213> ORGANISM: Artificial Sequence
<220> FEATURE:
<223> OTHER INFORMATION: FGF2-derived peptide (ERGVVSIKGV)

<400> SEQUENCE: 38

Glu Arg Gly Val Val Ser Ile Lys Gly Val
1               5                   10

<210> SEQ ID NO 39
<211> LENGTH: 14
<212> TYPE: PRT
<213> ORGANISM: Artificial Sequence
<220> FEATURE:
<223> OTHER INFORMATION: FGF2-derived peptide (WYVALKRTGQYKLG)

<400> SEQUENCE: 39

Trp Tyr Val Ala Leu Lys Arg Thr Gly Gln Tyr Lys Leu Gly
1               5                   10

<210> SEQ ID NO 40
<211> LENGTH: 11
<212> TYPE: PRT
<213> ORGANISM: Artificial Sequence
<220> FEATURE:
<223> OTHER INFORMATION: FGF2-derived peptide (HFKDPKRLYCK)

<400> SEQUENCE: 40

His Phe Lys Asp Pro Lys Arg Leu Tyr Cys Lys
1               5                   10

<210> SEQ ID NO 41
<211> LENGTH: 8
<212> TYPE: PRT
<213> ORGANISM: Artificial Sequence
<220> FEATURE:
<223> OTHER INFORMATION: FGF2-derived peptide (FLPMSAKS)

<400> SEQUENCE: 41

Phe Leu Pro Met Ser Ala Lys Ser
1               5

<210> SEQ ID NO 42
<211> LENGTH: 8
<212> TYPE: PRT
<213> ORGANISM: Artificial Sequence
<220> FEATURE:
<223> OTHER INFORMATION: FGF2-derived peptide (KTGPGQKA)

<400> SEQUENCE: 42

Lys Thr Gly Pro Gly Gln Lys Ala
1               5

<210> SEQ ID NO 43
<211> LENGTH: 16
<212> TYPE: PRT
<213> ORGANISM: Artificial Sequence
```

```
<220> FEATURE:
<223> OTHER INFORMATION: FGF4-derived (SRFFVAMSSKGKLYGS)

<400> SEQUENCE: 43

Ser Arg Phe Phe Val Ala Met Ser Ser Lys Gly Lys Leu Tyr Gly Ser
1               5                   10                  15

<210> SEQ ID NO 44
<211> LENGTH: 14
<212> TYPE: PRT
<213> ORGANISM: Artificial Sequence
<220> FEATURE:
<223> OTHER INFORMATION: FGF4-derived (MFIALSKNGKTKKG)

<400> SEQUENCE: 44

Met Phe Ile Ala Leu Ser Lys Asn Gly Lys Thr Lys Lys Gly
1               5                   10

<210> SEQ ID NO 45
<211> LENGTH: 12
<212> TYPE: PRT
<213> ORGANISM: Artificial Sequence
<220> FEATURE:
<223> OTHER INFORMATION: TGFB-derived peptide (LTGKNFPMFHRN)

<400> SEQUENCE: 45

Leu Thr Gly Lys Asn Phe Pro Met Phe His Arg Asn
1               5                   10

<210> SEQ ID NO 46
<211> LENGTH: 12
<212> TYPE: PRT
<213> ORGANISM: Artificial Sequence
<220> FEATURE:
<223> OTHER INFORMATION: TGFB-derived peptide (MHRMPSFLPTTL)

<400> SEQUENCE: 46

Met His Arg Met Pro Ser Phe Leu Pro Thr Thr Leu
1               5                   10

<210> SEQ ID NO 47
<211> LENGTH: 20
<212> TYPE: PRT
<213> ORGANISM: Artificial Sequence
<220> FEATURE:
<223> OTHER INFORMATION: WNT-derived peptide (LCCGRGHRTRTQRVTERCNC)

<400> SEQUENCE: 47

Leu Cys Cys Gly Arg Gly His Arg Thr Arg Thr Gln Arg Val Thr Glu
1               5                   10                  15

Arg Cys Asn Cys
            20

<210> SEQ ID NO 48
<211> LENGTH: 20
<212> TYPE: PRT
<213> ORGANISM: Artificial Sequence
<220> FEATURE:
<223> OTHER INFORMATION: WNT-derived peptide (LGTQGRLCNKTSEGMDGCEL)

<400> SEQUENCE: 48

Leu Gly Thr Gln Gly Arg Leu Cys Asn Lys Thr Ser Glu Gly Met Asp
1               5                   10                  15

Gly Cys Glu Leu
            20
```

```
<210> SEQ ID NO 49
<211> LENGTH: 10
<212> TYPE: PRT
<213> ORGANISM: Artificial Sequence
<220> FEATURE:
<223> OTHER INFORMATION: LIF-derived peptide (IVPLLLLVLH)

<400> SEQUENCE: 49

Ile Val Pro Leu Leu Leu Val Leu His
1               5                   10

<210> SEQ ID NO 50
<211> LENGTH: 18
<212> TYPE: PRT
<213> ORGANISM: Artificial Sequence
<220> FEATURE:
<223> OTHER INFORMATION: LIF-derived peptide (YTAQGEPFPNNVEKLCAP)

<400> SEQUENCE: 50

Tyr Thr Ala Gln Gly Glu Pro Phe Pro Asn Asn Val Glu Lys Leu Cys
1               5                   10                  15

Ala Pro

<210> SEQ ID NO 51
<211> LENGTH: 10
<212> TYPE: PRT
<213> ORGANISM: Artificial Sequence
<220> FEATURE:
<223> OTHER INFORMATION: Laminin-derived peptide (RNIAEIIKDI)

<400> SEQUENCE: 51

Arg Asn Ile Ala Glu Ile Ile Lys Asp Ile
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Cadherin-derived peptide (LFSHAVSSNG)

<400> SEQUENCE: 52

Leu Phe Ser His Ala Val Ser Ser Asn Gly
1               5                   10

<210> SEQ ID NO 53
<211> LENGTH: 6
<212> TYPE: PRT
<213> ORGANISM: Artificial Sequence
<220> FEATURE:
<223> OTHER INFORMATION: Cadherin-derived peptide (ADTPPV)

<400> SEQUENCE: 53

Ala Asp Thr Pro Pro Val
1               5

<210> SEQ ID NO 54
<211> LENGTH: 5
<212> TYPE: PRT
<213> ORGANISM: Artificial Sequence
<220> FEATURE:
<223> OTHER INFORMATION: Cadherin-derived peptide (DQNDN)

<400> SEQUENCE: 54

Asp Gln Asn Asp Asn
1               5
```

<210> SEQ ID NO 55
<211> LENGTH: 10
<212> TYPE: PRT
<213> ORGANISM: Artificial Sequence
<220> FEATURE:
<223> OTHER INFORMATION: Laminin-derived peptide (LRAHAVDING)

<400> SEQUENCE: 55

Leu Arg Ala His Ala Val Asp Ile Asn Gly
1               5                   10

<210> SEQ ID NO 56
<211> LENGTH: 16
<212> TYPE: PRT
<213> ORGANISM: Artificial Sequence
<220> FEATURE:
<223> OTHER INFORMATION: Vitronectin-derived peptide (KKQRFRHRNRKGYRSG)

<400> SEQUENCE: 56

Lys Lys Gln Arg Phe Arg His Arg Asn Arg Lys Gly Tyr Arg Ser Gly
1               5                   10                  15

<210> SEQ ID NO 57
<211> LENGTH: 7
<212> TYPE: PRT
<213> ORGANISM: Artificial Sequence
<220> FEATURE:
<223> OTHER INFORMATION: Laminin peptide (RYVVLPR)

<400> SEQUENCE: 57

Arg Tyr Val Val Leu Pro Arg
1               5

<210> SEQ ID NO 58
<211> LENGTH: 6
<212> TYPE: PRT
<213> ORGANISM: Artificial Sequence
<220> FEATURE:
<223> OTHER INFORMATION: Laminin peptide (GIIFFL)

<400> SEQUENCE: 58

Gly Ile Ile Phe Phe Leu
1               5

<210> SEQ ID NO 59
<211> LENGTH: 16
<212> TYPE: PRT
<213> ORGANISM: Artificial Sequence
<220> FEATURE:
<223> OTHER INFORMATION: Antimicrobial peptide (KLWKKWAKKWLKLWKA)

<400> SEQUENCE: 59

Lys Leu Trp Lys Lys Trp Ala Lys Lys Trp Leu Lys Leu Trp Lys Ala
1               5                   10                  15

<210> SEQ ID NO 60
<211> LENGTH: 11
<212> TYPE: PRT
<213> ORGANISM: Artificial Sequence
<220> FEATURE:
<223> OTHER INFORMATION: Antimicrobial peptide (FALALKALKKL)

<400> SEQUENCE: 60

Phe Ala Leu Ala Leu Lys Ala Leu Lys Lys Leu
1               5                   10

```
<210> SEQ ID NO 61
<211> LENGTH: 12
<212> TYPE: PRT
<213> ORGANISM: Artificial Sequence
<220> FEATURE:
<223> OTHER INFORMATION: Antimicrobial peptide (ILRWPWWPWRRK)

<400> SEQUENCE: 61

Ile Leu Arg Trp Pro Trp Trp Pro Trp Arg Arg Lys
1               5                   10

<210> SEQ ID NO 62
<211> LENGTH: 12
<212> TYPE: PRT
<213> ORGANISM: Artificial Sequence
<220> FEATURE:
<223> OTHER INFORMATION: Antimicrobial peptide (AKRHHGYKRKFH)

<400> SEQUENCE: 62

Ala Lys Arg His His Gly Tyr Lys Arg Lys Phe His
1               5                   10

<210> SEQ ID NO 63
<211> LENGTH: 15
<212> TYPE: PRT
<213> ORGANISM: Artificial Sequence
<220> FEATURE:
<223> OTHER INFORMATION: Antimicrobial peptide (KWKLFKKIGAVLKVL)

<400> SEQUENCE: 63

Lys Trp Lys Leu Phe Lys Lys Ile Gly Ala Val Leu Lys Val Leu
1               5                   10                  15

<210> SEQ ID NO 64
<211> LENGTH: 15
<212> TYPE: PRT
<213> ORGANISM: Artificial Sequence
<220> FEATURE:
<223> OTHER INFORMATION: Antimicrobial peptide (LVKLVAGIKKFLKWK)

<400> SEQUENCE: 64

Leu Val Lys Leu Val Ala Gly Ile Lys Lys Phe Leu Lys Trp Lys
1               5                   10                  15

<210> SEQ ID NO 65
<211> LENGTH: 25
<212> TYPE: PRT
<213> ORGANISM: Artificial Sequence
<220> FEATURE:
<223> OTHER INFORMATION: Antimicrobial peptide
      (IWSILAPLGTTLVKLVAGIGQQKRK)

<400> SEQUENCE: 65

Ile Trp Ser Ile Leu Ala Pro Leu Gly Thr Thr Leu Val Lys Leu Val
1               5                   10                  15

Ala Gly Ile Gly Gln Gln Lys Arg Lys
            20                  25

<210> SEQ ID NO 66
<211> LENGTH: 20
<212> TYPE: PRT
<213> ORGANISM: Artificial Sequence
<220> FEATURE:
<223> OTHER INFORMATION: Antimicrobial peptide (GIGAVLKVLTTGLPALISWI)

<400> SEQUENCE: 66
```

```
Gly Ile Gly Ala Val Leu Lys Val Leu Thr Thr Gly Leu Pro Ala Leu
1               5                   10                  15

Ile Ser Trp Ile
            20

<210> SEQ ID NO 67
<211> LENGTH: 16
<212> TYPE: PRT
<213> ORGANISM: Artificial Sequence
<220> FEATURE:
<223> OTHER INFORMATION: Antimicrobial peptide (SWLSKTAKKGAVLKVL)

<400> SEQUENCE: 67

Ser Trp Leu Ser Lys Thr Ala Lys Lys Gly Ala Val Leu Lys Val Leu
1               5                   10                  15

<210> SEQ ID NO 68
<211> LENGTH: 11
<212> TYPE: PRT
<213> ORGANISM: Artificial Sequence
<220> FEATURE:
<223> OTHER INFORMATION: Antimicrobial peptide (KKLFKKILKYL)

<400> SEQUENCE: 68

Lys Lys Leu Phe Lys Lys Ile Leu Lys Tyr Leu
1               5                   10

<210> SEQ ID NO 69
<211> LENGTH: 16
<212> TYPE: PRT
<213> ORGANISM: Artificial Sequence
<220> FEATURE:
<223> OTHER INFORMATION: Antimicrobial peptide (GLKKLISWIKRAAQQG)

<400> SEQUENCE: 69

Gly Leu Lys Lys Leu Ile Ser Trp Ile Lys Arg Ala Ala Gln Gln Gly
1               5                   10                  15

<210> SEQ ID NO 70
<211> LENGTH: 39
<212> TYPE: PRT
<213> ORGANISM: Artificial Sequence
<220> FEATURE:
<223> OTHER INFORMATION: Antimicrobial peptide
      (GWLKKIGKKIERVGQHTRDATIQGLGIAQQAANVAATAR)

<400> SEQUENCE: 70

Gly Trp Leu Lys Lys Ile Gly Lys Lys Ile Glu Arg Val Gly Gln His
1               5                   10                  15

Thr Arg Asp Ala Thr Ile Gln Gly Leu Gly Ile Ala Gln Gln Ala Ala
            20                  25                  30

Asn Val Ala Ala Thr Ala Arg
            35

<210> SEQ ID NO 71
<211> LENGTH: 13
<212> TYPE: PRT
<213> ORGANISM: Artificial Sequence
<220> FEATURE:
<223> OTHER INFORMATION: FGF2-derived peptide (WYVALKRTGQKLG)

<400> SEQUENCE: 71

Trp Tyr Val Ala Leu Lys Arg Thr Gly Gln Lys Leu Gly
1               5                   10
```

```
<210> SEQ ID NO 72
<211> LENGTH: 12
<212> TYPE: PRT
<213> ORGANISM: Artificial Sequence
<220> FEATURE:
<223> OTHER INFORMATION: Laminin-derived peptide (THRPPMWSPVWP)

<400> SEQUENCE: 72

Thr His Arg Pro Pro Met Trp Ser Pro Val Trp Pro
1               5                   10

<210> SEQ ID NO 73
<211> LENGTH: 10
<212> TYPE: PRT
<213> ORGANISM: Artificial Sequence
<220> FEATURE:
<223> OTHER INFORMATION: FGF2-derived peptide (KTGPQKKAIL)

<400> SEQUENCE: 73

Lys Thr Gly Pro Gln Lys Lys Ala Ile Leu
1               5                   10

<210> SEQ ID NO 74
<211> LENGTH: 5
<212> TYPE: PRT
<213> ORGANISM: Artificial Sequence
<220> FEATURE:
<223> OTHER INFORMATION: integrin-derived peptide (IKVAV)

<400> SEQUENCE: 74

Ile Lys Val Ala Val
1               5

<210> SEQ ID NO 75
<211> LENGTH: 4
<212> TYPE: PRT
<213> ORGANISM: Artificial Sequence
<220> FEATURE:
<221> NAME/KEY: any amino acid or none
<222> LOCATION: (3)..(4)
<223> OTHER INFORMATION: integrin-derived peptide (NRW-)

<400> SEQUENCE: 75

Asn Arg Trp Xaa
1

<210> SEQ ID NO 76
<211> LENGTH: 4
<212> TYPE: PRT
<213> ORGANISM: Artificial Sequence
<220> FEATURE:
<221> NAME/KEY: any amino acid or none
<222> LOCATION: (3)..(4)
<223> OTHER INFORMATION: integrin-derived peptide (TWY-)

<400> SEQUENCE: 76

Thr Trp Tyr Xaa
1

<210> SEQ ID NO 77
<211> LENGTH: 5
<212> TYPE: PRT
<213> ORGANISM: Artificial Sequence
<220> FEATURE:
<223> OTHER INFORMATION: integrin-derived peptide (YIGSR)

<400> SEQUENCE: 77

Tyr Ile Gly Ser Arg
```

```
<210> SEQ ID NO 78
<211> LENGTH: 6
<212> TYPE: PRT
<213> ORGANISM: Artificial Sequence
<220> FEATURE:
<223> OTHER INFORMATION: integrin-derived peptide (GLPGER)

<400> SEQUENCE: 78

Gly Leu Pro Gly Glu Arg
1               5

<210> SEQ ID NO 79
<211> LENGTH: 6
<212> TYPE: PRT
<213> ORGANISM: Artificial Sequence
<220> FEATURE:
<223> OTHER INFORMATION: integrin-derived peptide (GFPGER)

<400> SEQUENCE: 79

Gly Phe Pro Gly Glu Arg
1               5

<210> SEQ ID NO 80
<211> LENGTH: 4
<212> TYPE: PRT
<213> ORGANISM: Artificial Sequence
<220> FEATURE:
<223> OTHER INFORMATION: integrin-derived peptide (DGEA)

<400> SEQUENCE: 80

Asp Gly Glu Ala
1

<210> SEQ ID NO 81
<211> LENGTH: 5
<212> TYPE: PRT
<213> ORGANISM: Artificial Sequence
<220> FEATURE:
<221> NAME/KEY: any amino acid or none
<222> LOCATION: (4)..(5)
<223> OTHER INFORMATION: integrin-derived peptide (GEFY-)

<400> SEQUENCE: 81

Gly Glu Phe Tyr Xaa
1               5
```